US008927590B2

(12) United States Patent
Alimardanov et al.

(10) Patent No.: US 8,927,590 B2
(45) Date of Patent: Jan. 6, 2015

(54) SYNTHESIS OF PYRROLIDINE COMPOUNDS

(75) Inventors: Asaf R. Alimardanov, Nanuet, NY (US); Lalitha Krishnan, Suffern, NY (US); Maotang Zhou, Cedar Knolls, NJ (US); Ting-Zhong Wang, Pomona, NY (US); Jianxin Ren, Nanuet, NY (US); John Leo Considine, Bridgewater, NJ (US); Charles C. Wu, Denville, NJ (US); Jason Brazzillo, Cortlandt Manor, NY (US); Panolil Raveendranath, Monroe, NY (US); Girija Raveendranath, legal representative, Monroe, NY (US); Vijay Raveendranath, legal representative, Albany, NY (US); Sanjay Raveendranath, legal representative, Monroe, NY (US); Karen Sutherland, New City, NY (US); Mahmoud Mirmehrabi, Laval (CA); Subodh S. Deshmukh, White Plains, NY (US)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 13/593,110

(22) Filed: Aug. 23, 2012

(65) Prior Publication Data

US 2013/0053344 A1  Feb. 28, 2013

Related U.S. Application Data

(63) Continuation of application No. 12/690,043, filed on Jan. 19, 2010, now abandoned, which is a continuation of application No. 12/005,118, filed on Dec. 20, 2007, now abandoned.

(60) Provisional application No. 60/876,290, filed on Dec. 21, 2006.

(51) Int. Cl.
*A61K 31/40* (2006.01)
*C07D 207/02* (2006.01)
*C07D 207/16* (2006.01)

(52) U.S. Cl.
CPC .................................. *C07D 207/16* (2013.01)
USPC .......................... 514/423; 548/533

(58) Field of Classification Search
USPC .......................... 514/423; 548/533
See application file for complete search history.

(56) References Cited

U.S. PATENT DOCUMENTS

| 4,780,528 | A | 10/1988 | Takemoto et al. |
| 4,849,525 | A | 7/1989 | Weller, III et al. |
| 5,120,859 | A | 6/1992 | Webb |
| 5,707,991 | A | 1/1998 | Capet et al. |
| 7,622,496 | B2 | 11/2009 | Larsen et al. |
| 2005/0203143 | A1 | 9/2005 | Breslin et al. |
| 2007/0149460 | A1 | 6/2007 | Larsen et al. |
| 2007/0232574 | A1 | 10/2007 | Galey et al. |

FOREIGN PATENT DOCUMENTS

| CN | 1528745 | 9/2004 |
| DE | 3831936 | 4/1989 |
| EP | 0071544 B1 | 2/1983 |
| EP | 0132304 B1 | 1/1985 |
| EP | 0052291 B1 | 7/1985 |
| EP | 0175266 B1 | 3/1986 |
| EP | 0254032 A2 | 1/1988 |
| EP | 0566157 A1 | 10/1993 |
| EP | 0672700 B1 | 9/1995 |
| EP | 1227805 B1 | 5/2005 |
| EP | 1604977 A1 | 12/2005 |
| GB | 2159160 | 11/1985 |
| WO | WO 95/13069 | 5/1995 |
| WO | WO 96/09820 | 4/1996 |
| WO | WO 97/36873 | 10/1997 |
| WO | WO 98/10653 | 3/1998 |
| WO | WO 98/17679 | 4/1998 |
| WO | WO 98/25897 | 6/1998 |
| WO | WO 99/09991 | 3/1999 |
| WO | WO 00/23421 | 4/2000 |
| WO | WO 01/07436 | 2/2001 |
| WO | WO 01/26644 | 4/2001 |
| WO | WO 01/34594 | 5/2001 |
| WO | WO 01/62775 | 8/2001 |
| WO | WO 01/74796 | 10/2001 |
| WO | WO 01/79162 | 10/2001 |
| WO | WO 01/83517 | 11/2001 |
| WO | WO 02/08244 | 1/2002 |
| WO | WO 02/08251 | 1/2002 |
| WO | WO 02/08256 | 1/2002 |
| WO | WO 02/30421 | 4/2002 |
| WO | WO 02/30462 | 4/2002 |
| WO | WO 02/39976 | 5/2002 |
| WO | WO 02/077017 | 10/2002 |
| WO | WO 02/089738 | 11/2002 |
| WO | WO 03/062228 | 7/2003 |

(Continued)

OTHER PUBLICATIONS

Berree et al., "N-Boc ethyl oxamate: a new nitrogen nucleophile for use in mitsunobu reactions" *Tetrahedron Lett.* 39:8275-8276 (1998).
Bhagwat et al., "4-Substituted proline derivatives that inhibit angiotensin converting enzyme and neutral endopeptidase 24.11" *Bioorg. Med. Chem. Lett.* 4:2673-2676 (1994).
Bridges et al., "Conformationally defined neurotransmitter analogues. Selective inhibition of glutamate uptake by one pyrrolidine-2,4-dicarboxylate diastereomer" *J. Med. Chem.* 34:717-725 (1991).
Communication from the European Patent Office for European Patent Application No. 07 867 854.7-2117, dated Mar. 10, 2010.

(Continued)

*Primary Examiner* — Samantha Shterengarts
(74) *Attorney, Agent, or Firm* — Kristina Bieker-Brady; Clark & Elbing LLP

(57) ABSTRACT

Provided are methods for the preparation of certain substituted pyrrolidine compounds, forms of (2S,4R)-1-(2-aminoacetyl)-4-benzamidopyrrolidine-2-carboxylic acid hydrochloride, and methods for preparing and using these forms.

3 Claims, 7 Drawing Sheets

(56) References Cited

FOREIGN PATENT DOCUMENTS

| WO | WO 03/062265 | 7/2003 |
|----|----|----|
| WO | WO 03/072528 | 9/2003 |
| WO | WO 2004/005248 | 1/2004 |
| WO | WO 2004/020599 | 3/2004 |
| WO | WO 2004/045518 | 6/2004 |
| WO | WO 2004/087646 | 10/2004 |
| WO | WO 2004/099134 | 11/2004 |
| WO | WO 2005/037214 | 4/2005 |
| WO | WO 2005/085197 | 9/2005 |
| WO | WO 2005/095403 | 10/2005 |
| WO | WO 2006/020276 | 2/2006 |
| WO | WO 2006/114401 | 11/2006 |
| WO | WO 2008/079266 | 7/2008 |

OTHER PUBLICATIONS

Communication from the European Patent Office for European Patent Application No. 07 867 854.7-2117, dated Feb. 1, 2011.
Database Registry, Database Accession No. 90559-49-2 (1984).
English language abstract for CN 1528745.
English language abstract for EP 0672700 B1.
Gangamani et al., "Synthesis of Nalpha-(Purinyl/Pyrimidinyl acetyl)-4-Aminoproline Diastereomers with Potential Use in PNA Synthesis" *Tetrahedron* 52:15017-15030 (1996).
Gregson et al., "Linker length modulates DNA cross-linking reactivity and cytotoxic potency of C8/C8' ether-linked C2-exo-unsaturated pyrrolo[2,1-c][1,4]benzodiazepine (PBD) dimers" *J. Med. Chem.* 47:1161-1174 (2004).
International Search Report issued in International Application No. PCT/US2006/048790, mailed Sep. 27, 2007.
International Search Report issued in International Application No. PCT/US2007/026002, mailed Sep. 17, 2008.
Khankari, Rajendra K. Pharmaceutical Hydrates. Thermochimica Acta. 248:61-79 (1995).
Neiss et al. CAPLUS Accession No. 479371 (1986).
Office Action mailed May 9, 2008 in U.S. Patent No. 7,622,496, filing date Dec. 21, 2006.
Watkins et al., "The relationship between physiochemical properties, in vitro activity and pharmacokinetic profiles of analogues of diamine-containing efflux pump inhibitors" *Bioorg. Med. Chem. Lett.* 13:4241-4244 (2003).

SYNTHESIS OF PYRROLIDINE COMPOUNDS

CROSS-REFERENCE TO RELATED APPLICATIONS

This application is a continuation of U.S. application Ser. No. 12/690,043, filed on Jan. 19, 2010, which is a continuation of U.S. application Ser. No. 12/005,118, filed Dec. 20, 2007, which, in turn, claims benefit from U.S. Provisional Application No. 60/876,290, filed on Dec. 21, 2006, each of which is hereby incorporated by reference.

STATEMENT UNDER 35 U.S.C. §103(c)(2)(C)

The claimed invention was made as a result of activities undertaken within the scope of a joint research agreement between Zealand Pharma A/S and Wyeth.

Provided are certain pyrrolidine compounds, compositions thereof, and methods for their preparation and use.

Generally, gap junctions are specialized regions of the cell membrane that contain clusters of hundreds to thousands of densely packed channels that directly connect the cytoplasm of two adjacent cells. The gap junction channels are composed of two hemichannels, or connexons, provided by each of two neighboring cells. Each connexon, in turn, is made up of six proteins called connexins.

There is increasing recognition that intercellular communication facilitated by gap junctions is essential for cellular homeostasis, proliferation and differentiation. Those structures are thought to be a route for coupling cells and permitting "cross-talk." The cross-talk between gap junctions is referred to as "gap junctional intercellular communication" (GJIC).

In the heart, conduction of electrical impulses takes place through gap junctions. Abnormal GJIC has been linked to a variety of disease states, including heart disease. For example, it has been shown that mice heterozygous for the Cx43 gene, which codes for a specific ventricular connexin, develop spontaneous ventricular arrhythmias and suffer from sudden cardiac death. Reduced expression of Cx43 in heterozygous mice is directly linked to an increased incidence of ventricular arrhythmias during ischemia. Several other studies have shown reduced expression or altered distribution of Cx43 in chronically ischemic, hibernating, or hypertrophied hearts.

Several peptides that influence GJIC have been identified, including antiarrhythmic peptides AAP, AAP10; and HP5. However, those peptides exhibit undesirable characteristics, including low stability, short half-life, and a lack of oral bioavailability.

The compound (2S,4R)-1-(2-aminoacetyl)-4-benzamidopyrrolidine-2-carboxylic acid:

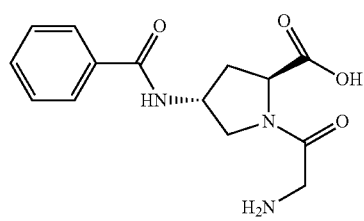 [SMILES: NCC(=O)N1C[C@H](NC(=O)c2ccccc2)C[C@H]1C(=O)O]

restores and maintains the gap junction integrity between cell membranes and is useful for the treatment of diseases associated with abnormal gap junction intercellular communications.

Provided is a method for preparing a compound of formula (I) or a salt thereof:

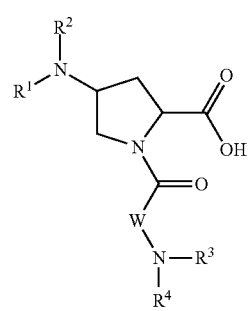

(I)

wherein:
one of $R^1$ and $R^2$ is hydrogen or $C_1$-$C_6$ alkyl, and the other is —C(O)$R^5$;
  wherein $R^5$ is chosen from:
    optionally substituted $C_6$-$C_{10}$ aryl;
    optionally substituted heteroaryl including 5-10 atoms;
    optionally substituted $C_1$-$C_{20}$ alkyl;
    optionally substituted $C_1$-$C_{20}$ haloalkyl;
    optionally substituted $C_7$-$C_{12}$ aralkyl;
    optionally substituted heteroaralkyl including 6-12 atoms;
    optionally substituted $C_3$-$C_{10}$ cycloalkyl; and
    optionally substituted $C_3$-$C_{10}$ cycloalkenyl;
  W is $C_{1-6}$ alkylene; and
  $R^3$ and $R^4$ may be the same or different and are each independently chosen from hydrogen, optionally substituted $C_1$-$C_6$ alkyl, —C(O)O$R^6$, and —C(O)$R^9$;
    wherein $R^6$ is optionally substituted $C_1$-$C_{20}$ alkyl; and
    wherein $R^9$ is chosen from
      hydrogen;
      optionally substituted $C_6$-$C_{10}$ aryl;
      optionally substituted heteroaryl including 5-10 atoms;
      optionally substituted $C_1$-$C_{20}$ alkyl;
      optionally substituted $C_3$-$C_{10}$ cycloalkyl; and
      optionally substituted heterocycloalkyl including 5-10 atoms;

the method comprising:
  converting a compound of formula (II) or a salt thereof:

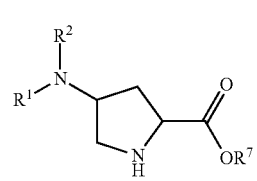

(II)

wherein:

$R^7$ is chosen from hydrogen and optionally substituted $C_1$-$C_6$ alkyl; to a compound of formula (III) or a salt thereof:

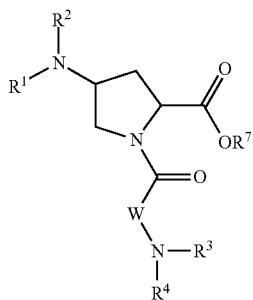

(III)

and, where $R^7$ in formula (III) is optionally substituted $C_1$-$C_6$ alkyl, reacting the compound of formula (III) with a metal hydroxide or other suitable base to provide a compound of formula (I) or a salt thereof. The conversion of the a compound of formula (II) or a salt thereof to a compound of formula (III) or a salt thereof may be performed by acylation in known manner. In particular the conversion may be carried out by reacting the compound of formula (II) with a compound having the formula (IV)

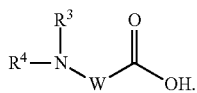

(IV)

wherein W, $R^3$ and $R^4$ are as defined herein or a reactive derivative thereof, for instance, a mixed anhydride thereof.

Also provided is a composition comprising (1) a compound of formula (I) or a salt thereof

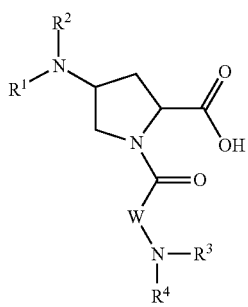

(I)

and/or a compound of formula (III) or a salt thereof

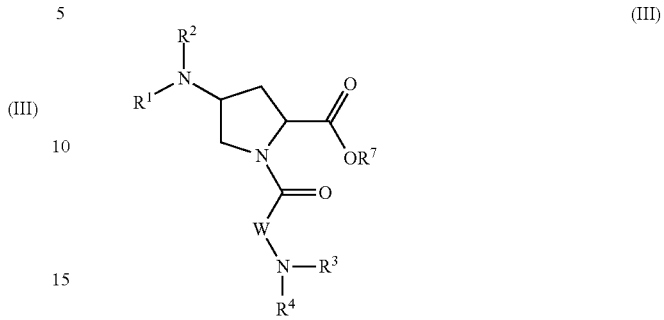

(III)

wherein one of $R^1$ and $R^2$ is hydrogen or $C_1$-$C_6$ alkyl, and the other is —C(O)$R^5$;

wherein $R^5$ is chosen from:

optionally substituted $C_6$-$C_{10}$ aryl;
optionally substituted heteroaryl including 5-10 atoms;
optionally substituted $C_1$-$C_{20}$ alkyl;
optionally substituted $C_1$-$C_{20}$ haloalkyl;
optionally substituted $C_7$-$C_{12}$ aralkyl;
optionally substituted heteroaralkyl including 6-12 atoms;
optionally substituted $C_3$-$C_{10}$ cycloalkyl; and
optionally substituted $C_3$-$C_{10}$ cycloalkenyl;

W is $C_{1-6}$ alkylene;

$R^3$ and $R^4$ may be the same or different and are each independently chosen from hydrogen, optionally substituted $C_1$-$C_6$ alkyl, —C(O)O$R^6$, and —C(O)$R^9$;

wherein $R^6$ is optionally substituted $C_1$-$C_{20}$ alkyl; and
wherein $R^9$ is chosen from
hydrogen;
optionally substituted $C_6$-$C_{10}$ aryl;
optionally substituted heteroaryl including 5-10 atoms;
optionally substituted $C_1$-$C_{20}$ alkyl;
optionally substituted $C_3$-$C_{10}$ cycloalkyl; and
optionally substituted heterocycloalkyl including 5-10 atoms; and $R^7$ is chosen from hydrogen and optionally substituted $C_1$-$C_6$ alkyl; and (2) a detectable amount of one or more compounds selected from:

N-((7R,8aS)-1,4-dioxooctahydropyrrolo[1,2-a]pyrazin-7-yl)benzamide or a salt thereof, i.e., a compound of formula

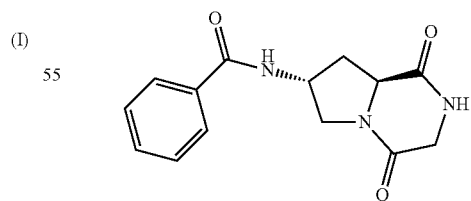

or a salt thereof;
triphenylphosphine;
triphenylphosphine oxide;
a hydrazine dicarboxylate;
triethylamine;
benzotriazole;

(2S,4R)-4-benzamido-1-(2-(tert-butylamino)acetyl)pyrrolidine-2-carboxylic acid or a salt thereof, i.e., a compound of formula:

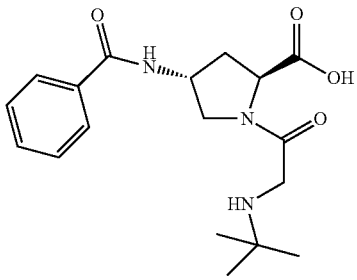

or a salt thereof;
and a compound of formula (II) or a salt thereof:

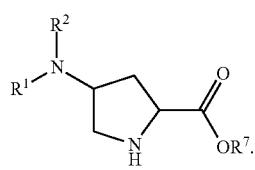

Also provided is a compound that is (2S,4R)-1-(2-aminoacetyl)-4-benzamidopyrrolidine-2-carboxylic acid hydrochloride.

Also provided is a compound that is (2S,4R)-1-(2-aminoacetyl)-4-benzamidopyrrolidine-2-carboxylic acid hydrochloride monohydrate.

Also provided is a method for preparing (2S,4R)-1-(2-aminoacetyl)-4-benzamidopyrrolidine-2-carboxylic acid hydrochloride monohydrate, comprising providing a solution of (2S,4R)-1-(2-aminoacetyl)-4-benzamidopyrrolidine-2-carboxylic acid hydrochloride in a crystallization medium, wherein the crystallization medium comprises at least one water-miscible organic solvent and water, and maintaining the solution for a time and under conditions suitable for forming the (2S,4R)-1-(2-aminoacetyl)-4-benzamidopyrrolidine-2-carboxylic acid hydrochloride monohydrate.

Also provided is a pharmaceutical formulation comprising one or more pharmaceutically acceptable carriers and a compound described herein.

Also provided is a method for treating a condition selected from cardiovascular disease; osteoporosis; inflammation of airway epithelium; disorders of alveolar tissue; bladder incontinence; impaired hearing; endothelial lesions; Type I or Type II diabetes; diabetic retinopathy; diabetic neuropathy; atherosclerosis; CNS related conditions; seizures; ischemia; dental tissue disorders; kidney diseases; anaemia; leukopenia; thrombocytopenia; pancytopenia; superficial wounds; deep wounds resulting from trauma; bone fractures; erectile dysfunction; urinary bladder incontinence; neuropathic pain; subchronic and chronic inflammation; cancer; failure of bone marrow; stem cell transplantation; conditions arising during transplantation of cells and tissues; conditions arising during medical procedures; conditions caused by an excess of reactive oxygen species, free radicals or nitric oxide; diseases or disorders of pregnancy; female infertility; and stroke, comprising administering to a patient a therapeutically effective amount of the compound described herein or a pharmaceutical formulation described herein.

It is to be understood that both the general description and the detailed description are exemplary and explanatory only and are not restrictive of the invention, as claimed.

The accompanying drawings, which are incorporated in and constitute a part of this specification, illustrate several embodiments of the invention. Other aspects and embodiments will be apparent to those skilled in the art from the following detailed description.

Figure 1:
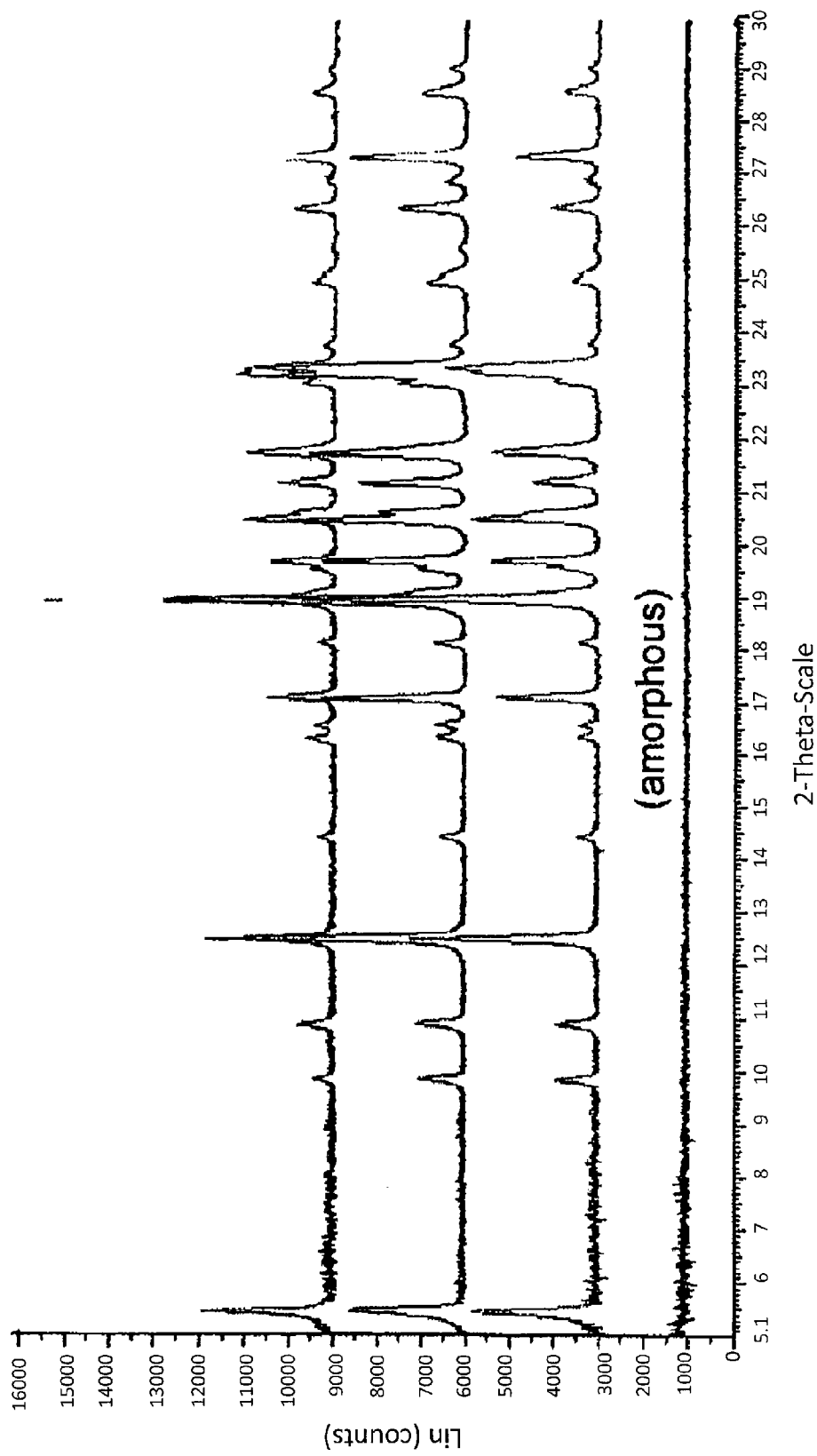
FIG. 1 shows the X-ray powder diffraction patterns of preparations of (2S,4R)-1-(2-aminoacetyl)-4-benzamidopyrrolidine-2-carboxylic acid hydrochloride as an amorphous solid and as a crystalline monohydrate.

As used herein, when any variable occurs more than one time in a chemical formula, its definition on each occurrence is independent of its definition at every other occurrence.

The following abbreviations and terms have the indicated meanings throughout:
Boc=t-butyloxy carbonyl
eq=equivalent
Et=ethyl
EtOAc=ethyl acetate
g=gram
HPLC=high performance liquid chromatography
h, hr, hrs=hour or hours
in=inch or inches
kg=kilogram
L=liter
LC=liquid chromatography
M=molar
Me=methyl
min=minute
ml or mL=milliliter
mmol=millimole
mol=mole
Ph=phenyl
ppm=parts per million
Pr=propyl
TEA=triethylamine As used in the present specification, the following words and phrases are generally intended to have the meanings as set forth below, except to the extent that the context in which they are used indicates otherwise.

As used herein, the term "alkyl" refers to a saturated hydrocarbon chain that may be a straight chain or branched chain, containing the indicated number of carbon atoms. For example, the term "$C_1$-$C_{20}$ alkyl" indicates that the group may be branched or unbranched, and may contain from 1 to 20 (inclusive) carbon atoms. Similarly, the term "$C_1$-$C_6$ alkyl" indicates that the group may be branched or unbranched, and may contain from 1 to 6 (inclusive) carbon atoms. Any atom may optionally be substituted. Non-limiting examples of alkyl groups include, for example, methyl, ethyl, and tert-butyl.

As used herein, the term "alkylene" refers to a bivalent alkyl radical, i.e., an alkyl radical having two points of attachment. For example, a methylene group is a —$CH_2$— group and an ethylene group is a —$CH_2CH_2$— group.

As used herein, the term "aralkyl" refers to an alkyl moiety wherein an alkyl hydrogen atom is replaced by an aryl group. One of the carbons of the alkyl moiety serves as the point of attachment of the aralkyl group to another moiety. The term "aralkyl" also includes groups wherein more than one hydrogen atom on an alkyl moiety has been replaced by an aryl group. Any ring or chain atom may optionally be substituted by one or more substituents. Non-limiting examples of "aralkyl" groups include benzyl, 2-phenylethyl (sometimes referred to as "phenethyl"), 3-phenylpropyl, benzhydryl (diphenylmethyl), and trityl (triphenylmethyl) groups.

As used herein, the term "aryl" refers to a $C_6$-$C_{14}$ (e.g., $C_6$-$C_{10}$, $C_6$) aromatic monocyclic ($C_6$), bicyclic ($C_{10}$), or tricyclic ($C_{14}$) hydrocarbon ring system. Any ring atom may optionally be substituted by one or more substituents. Aryl groups may also contain fused rings. Fused rings are rings that share a common carbon atom. Non-limiting examples of aryl moieties include phenyl, naphthyl, and anthracenyl.

As used herein, the term "converting" refers to one or more chemical transformations, which can be performed in situ, or with isolation of intermediate compounds. The transformations can include reacting the starting compounds or intermediates with additional reagents using techniques and protocols known in the art, including those described herein. Intermediates can be used with or without purification (e.g., filtration, distillation, sublimation, crystallization, trituration, solid phase extraction, chromatography).

As used herein, the term "cycloalkyl" refers to saturated monocyclic, bicyclic, tricyclic, or other polycyclic hydrocarbon groups. Any atom may optionally be substituted by one or more substituents. A ring carbon serves as the point of attachment of a cycloalkyl group to another moiety. Cycloalkyl groups may contain fused rings. Fused rings are rings that share a common carbon atom. Non-limiting examples of cycloalkyl moieties include cyclopropyl, cyclobutyl, cyclopentyl, cyclohexyl, cycloheptyl, adamantyl, and norbornyl (bicyclo[2.2.1]heptyl).

As used herein, the term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom may optionally be substituted by one or more substituents. Cycloalkenyl groups may contain fused rings. Fused rings are rings that share a common carbon atom. Non-limiting examples of cycloalkenyl moieties include cyclohexenyl, cyclohexadienyl, or norbornenyl.

As used herein, a "detectable amount" of a compound is intended to mean a sufficient amount to give positive identification but not necessarily quantitation of the compound by any suitable analytical technique, for example HPLC.

As used herein, the term "halo" or "halogen" refers to any radical of fluorine, chlorine, bromine or iodine.

As used herein, the term "haloalkyl" refers to an alkyl group wherein at least one hydrogen atom is replaced by halo. In some embodiments, more than one hydrogen atom (for example, 2, 3, 4, 5, 6, 7, 8, 9, 10, 11, 12, 13, 14, 15, 16, 17, 18, 19, 20, 21, 22, 23, 24, 25, 26, etc. hydrogen atoms) on an alkyl group may be replaced by more than one halogen (e.g., 2, 3, 4, 5, 6, 7, 8, 9, 10, 11, 12, 13, 14, 15, 16, 17, 18, 19, 20, 21, 22, 23, 24, 25, 26, etc. halogen atoms). In these embodiments, the hydrogen atoms may each be replaced by the same halogen (e.g., fluoro) or the hydrogen atoms may be replaced by a combination of different halogens (e.g., fluoro and chloro). The term "haloalkyl" also include alkyl moieties wherein all hydrogens have been replaced by halo (e.g., perhaloalkyl, such as trifluoromethyl).

As used herein, the term "heteroaralkyl" refers to an alkyl moiety wherein an alkyl hydrogen atom is replaced by a heteroaryl group. One of the carbons of the alkyl moiety serves as the point of attachment of the aralkyl group to another moiety. The term "heteroaralkyl" also includes groups wherein more than one hydrogen atom on an alkyl moiety has been replaced by a heteroaryl group. Any ring or chain atom may optionally be substituted by one or more substituents. Non-limiting examples of heteroaralkyl groups include 2-pyridylmethyl and 2-pyridylethyl.

As used herein, the term "heteroaryl" refers to an aromatic monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, wherein said heteroatoms are independently selected from O, N, or S (and mono and dioxides thereof, e.g., N→O$^-$, S(O), SO$_2$). Any atom may optionally be substituted by one or more substituents. Heteroaryl groups may contain fused rings. Fused rings are rings that share a common carbon atom. Non-limiting examples of heteroaryl groups include pyridyl, thienyl, furyl (furanyl), imidazolyl, indolyl, isoquinolyl, quinolyl and pyrrolyl.

As used herein, the term "heterocycloalkyl" refers to a saturated or partially unsaturated monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, wherein said heteroatoms are independently selected from O, N, or S (and mono and dioxides thereof, e.g., N→O$^-$, S(O), SO$_2$). Any atom may optionally be substituted by one or more substituents. Heteroaryl groups may contain fused rings. Fused rings are rings that share a common carbon atom. Non-limiting examples of heteroaryl groups include morpholinyl, piperidinyl, piperazinyl and pyrrolidinyl.

As used herein, the term "nitrogen protecting group" refers to a moiety which, when attached to a nitrogen atom of an acyclic or cyclic amino group (e.g., a pyrrolidine ring nitrogen atom), temporarily blocks that amino group so as to render it chemically inert. A nitrogen protecting group may also be introduced and removed (i.e., "deprotected") without complete destruction of the starting material and subsequent reaction product, respectively. Non-limiting examples of suitable protecting groups include those delineated herein. Other non-limiting examples of suitable protecting groups may be found in, e.g., T. W. Greene et al., *Protective Groups in Organic Synthesis*, John Wiley and Sons (1991).

As used herein, the expression "optionally substituted" when used in conjunction with any substituent described herein (e.g., $C_1$-$C_{20}$ alkyl or $C_1$-$C_{20}$ haloalkyl) means that any 1, 2, 3, 4, or 5 hydrogen atoms (and/or halo atoms in the case of a haloalkyl) may be replaced by a substituent independently chosen from NH$_2$, NH($C_1$-$C_6$ alkyl), N($C_1$-$C_6$ alkyl)$_2$, nitro; azido; hydroxy; oxo; thioxo; =NR; $C_1$-$C_{20}$ alkyl, $C_1$-$C_{20}$ haloalkyl, $C_2$-$C_{20}$ alkenyl; $C_2$-$C_{20}$ alkynyl; $C_3$-$C_{20}$ cycloalkyl; $C_3$-$C_{20}$ cycloalkenyl, heterocyclyl including 3-20 atoms; heterocycloalkenyl including 3-20 atoms; $C_7$-$C_{20}$ aralkyl; heteroaralkyl including 6-20 atoms; $C_1$-$C_{20}$ alkoxy;

$C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy; $C_7$-$C_{20}$ thioaralkoxy, thioheteroaralkoxy including 6-20 atoms; $C_3$-$C_{16}$ thiocycloalkoxy; $C_3$-$C_{20}$ thiocycloalkenyloxy; thioheterocyclyloxy including 3-20 atoms; or thioheterocycloalkenyloxy including 3-20 atoms; cyano; —C(O)R''; —C(O)OR''; —OC(O)R''; —C(O)NR°R$^p$; —NR$^q$C(O)R''; —OC(O)NR°R$^p$; —NR$^q$C(O)NR°R$^p$; —NR$^q$C(O)OR''; —S(O)$_n$R$^h$, wherein n is 1 or 2; —NR$^q$S(O)$_n$R$^h$, wherein n is 1 or 2; or —P(O)(OR°)(OR$^p$). R$^h$, R'', R°, R$^p$, R$^q$ are each independently hydrogen, $C_1$-$C_{20}$ alkyl, $C_6$-$C_{10}$ aryl, or $C_7$-$C_{20}$ aralkyl.

As used herein, the term "polymorphism" is defined as in the International Conference on Harmonization (ICH) Guideline Q6A Guideline: Specifications for New Drug Substances and Products: Chemical Substances, October 1999, and refers to the occurrence of different solid forms of the same drug substance. Polymorphism includes solvation products and amorphous forms. Amorphous forms consist of disordered arrangements of molecules and do not possess a distinguishable crystal lattice. Solvation products are crystalline solid adducts containing either stoichiometric or nonstoichiometric amounts of a solvent incorporated within the crystal structure. If the incorporated solvent is water, the solvates are also commonly known as hydrates.

As used herein, the term "reacting" or "contacting" refers to the bringing together of designated chemical reactants such that a chemical transformation takes place generating a compound different from any initially introduced into the system. Reacting or contacting can take place in the presence or absence of solvent.

As used herein, the term "salts" is derived from the combination of a compound and an organic or inorganic acid or base. The compounds described herein are useful in both free and salt form. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, Vol. 66, p. 1-19. The salts can be prepared in situ during the final isolation and purification of the compounds described herein or separately by reacting a free base function with a suitable organic acid.

Pharmaceutically acceptable salts of the compounds of the present teachings having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also can be formed. Similarly, when a compound of the present teachings contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, and camphorsulfonic as well as other known pharmaceutically acceptable acids. Amino acid addition salts can also be formed with amino acids such as lysine, glycine, or phenylalanine. Representative acid addition salts include hydrochloride salts. Other acceptable salts may be found through compendia listing compounds previously approved by the Food & Drug Administration.

As used herein, the term "solution" means a mixture of one or more solutes in one or more solvents. Solution is intended to encompass homogeneous mixtures as well as heterogeneous mixtures, such as slurries or other mixtures having a suspension of insoluble (not dissolved) material.

As used herein, the terms "solvent", "organic solvent" or "inert solvent" each mean a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions described herein are inert organic solvents. As used herein, the term "anti-solvent" means a substance that reduces the solubility of a solute in a solvent. In some embodiments, an antisolvent is one or more chemical liquids or mixtures thereof in which the compound to be purified exhibits a lower solubility than the solvent in which it is partially or entirely dissolved.

At various places in the present specification, substituents of compounds described herein are disclosed in groups or in ranges. It is specifically intended that the present teachings include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. For example, the term "$C_{1-6}$ alkyl" is also specifically intended to individually disclose methyl, ethyl, propyl, isopropyl, n-butyl, sec-butyl, isobutyl, etc.

The starting materials, intermediates, and products of the methods described herein may contain one, two, or more asymmetric centers and thus occur as racemates and racemic mixtures, single enantiomers, individual diastereomers and enantiomeric or diastereomeric mixtures. All such isomeric forms of these compounds are expressly included in the present disclosure. The compounds described herein may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present disclosure. The compounds described herein may also be represented in multiple tautomeric forms, in such instances, the present disclosure expressly includes all tautomeric forms of the compounds described herein, even though only a single tautomeric form may be represented. All such isomeric forms of such compounds are expressly included in the present disclosure.

The starting materials, intermediates, and products of the methods described herein each include a pyrrolidine ring that is substituted at the 2- and the 4-positions of the ring. For purposes of clarification, each of the following absolute ring stereochemistries is contemplated for the starting materials, intermediates, and products of the methods described herein: 2S,4R; 2R, 4S; 2S,4S, and 2R, 4R.

In some embodiments, any starting material, intermediate, or product of the methods described herein may occur as a stereoisomer mixture having at least about 60% (e.g., at least about 70%, at least about 75%, at least about 80%, at least about 85%, at least about 90%, at least about 95%, at least about 99%, greater than about 99%) of one of the four possible stereoisomers (e.g., 2S,4R; 2R, 4S; 2S,4S; or 2R, 4R). The starting material, intermediate, or product may be substantially free of its enantiomer and the other two possible stereoisomers. The starting material, intermediate, or product may be one of the four possible stereoisomers (e.g., 2S,4R or 2S,4S) in substantially pure form and be substantially free of its stereoisomers as well as other non-stereoisomer-related materials, e.g., solvents, reagents, reaction by-products and the like.

In some embodiments, any starting material, intermediate, or product of the methods described herein may occur as a stereoisomer mixture having at least about 60% (e.g., at least about 70%, at least about 75%, at least about 80%, at least about 85%, at least about 90%, at least about 95%, at least about 99%, greater than about 99%) of two of the four possible stereoisomers (e.g., R,R and S,S; R,S and S,R; R,R and S,R; R,R and R,S; S,S and S,R; or S,S and R,S).

It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

As used herein, unless otherwise expressly specified, all numbers such as those expressing values, ranges, amounts, or percentages may be read as if prefaced by the word "about", even if the term does not expressly appear.

The details of one or more embodiments of the present disclosure are set forth in the description below. Other features and advantages of the present disclosure will be apparent from the description and from the claims.

Provided is a method for preparing a compound of formula (I) or a salt thereof:

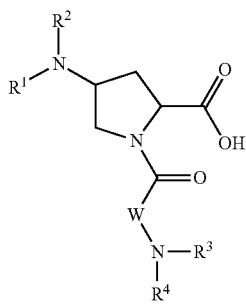

(I)

wherein:
one of $R^1$ and $R^2$ is hydrogen or $C_1$-$C_6$ alkyl, and the other is —C(O)$R^5$;
wherein $R^5$ is chosen from:
optionally substituted $C_6$-$C_{10}$ aryl;
optionally substituted heteroaryl including 5-10 atoms;
optionally substituted $C_1$-$C_{20}$ alkyl;
optionally substituted $C_1$-$C_{20}$ haloalkyl;
optionally substituted $C_7$-$C_{12}$ aralkyl;
optionally substituted heteroaralkyl including 6-12 atoms;
optionally substituted $C_3$-$C_{10}$ cycloalkyl; and
optionally substituted $C_3$-$C_{10}$ cycloalkenyl;

W is $C_{1-6}$ alkylene; and
$R^3$ and $R^4$ may be the same or different, and are each independently chosen from hydrogen, optionally substituted $C_1$-$C_6$ alkyl, —C(O)O$R^6$, and —C(O)$R^9$;
wherein $R^6$ is optionally substituted $C_1$-$C_{20}$ alkyl; and
wherein $R^9$ is chosen from
hydrogen;
optionally substituted $C_6$-$C_{10}$ aryl;
optionally substituted heteroaryl including 5-10 atoms;
optionally substituted $C_1$-$C_{20}$ alkyl;
optionally substituted $C_3$-$C_{10}$ cycloalkyl; and
optionally substituted heterocycloalkyl including 5-10 atoms;

the method comprising:
converting a compound of formula (II) or a salt thereof:

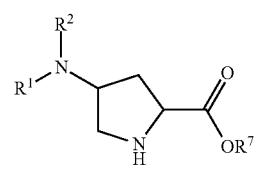

(II)

wherein:
$R^7$ is chosen from hydrogen and optionally substituted $C_1$-$C_6$ alkyl; to a compound of formula (III) or a salt thereof:

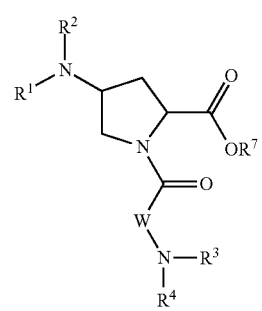

(III)

and, where $R^7$ in formula (III) is optionally substituted $C_1$-$C_6$ alkyl,
reacting the compound of formula (III) or a salt thereof with a metal hydroxide or other suitable base to provide a compound of formula (I) or a salt thereof.

In some embodiments, W in formula (I) is —CH$_2$—.
In some embodiments, each of $R^3$ and $R^4$ in formula (I) is hydrogen. In some embodiments, one of $R^3$ and $R^4$ is hydrogen, and the other is —C(O)O$R^6$. In other embodiments, one of $R^3$ and $R^4$ in formula (I) is hydrogen, and the other is —C(O)$R^9$.

In some embodiments, W in formula (I) is —CH$_2$—; and each of $R^3$ and $R^4$ in formula (I) is hydrogen.

In some embodiments, W in formula (I) is —CH$_2$—; and one of $R^3$ and $R^4$ in formula (I) is hydrogen, and the other is —C(O)O$R^6$. In some embodiments, $R^6$ in formula (I) is $C_1$-$C_6$ alkyl. In some embodiments, $R^6$ is tert-butyl. In some embodiments, $R^6$ is benzyl.

In some embodiments, W in formula (I) is —CH$_2$—; and one of $R^3$ and $R^4$ in formula (I) is hydrogen, and the other is —C(O)$R^9$. In some embodiments, $R^9$ in formula (I) is hydrogen. In some embodiments, $R^9$ in formula (I) is $C_1$-$C_6$ alkyl.

In some embodiments, $R^9$ in formula (I) is methyl. In some embodiments, $R^9$ in formula (I) is optionally substituted phenyl.

In some embodiments, $R^5$ in formula (I) is optionally substituted $C_6$-$C_{10}$ aryl. In some embodiments, $R^5$ is phenyl.

In some embodiments, $R^7$ is $C_1$-$C_6$ alkyl. In some embodiments, $R^7$ in formula (II) is $CH_3$.

In some embodiments, the —$NR^1R^2$ group and the —COOH group in formula (I) are trans with respect to one another. In some embodiments, the ring carbon attached to the —$NR^1R^2$ group has the R configuration, and the ring carbon attached to the —COOH group has the S configuration.

In some embodiments, the —$NR^1R^2$ group and the —$COOR^7$ group in formula (II) are trans with respect to one another. In some embodiments, the ring carbon attached to the —$NR^1R^2$ group has the R configuration, and the ring carbon attached to the —$COOR^7$ group has the S configuration.

The compound of formula (II) can be in the form of a free base or a salt (e.g., an HCl salt). In some embodiments, the compound of formula (II) can be free-based separately or in situ by treatment with the appropriate organic or inorganic base, in an organic solvent or a mixture of organic solvent and water; for example, by treatment with NaOH in a mixture of THF and water. In some embodiments, the solvent is methylene chloride ($CH_2Cl_2$), which can be exchanged with acetone for subsequent isolation. In some embodiments, triethylamine is used to neutralize the HCl salt of the compound of formula (II), which in some cases can minimize the likelihood of partial hydrolysis of the ester functionality (e.g., methyl ester) and generation of subsequent impurities.

In some embodiments, the metal hydroxide is a Group IA metal hydroxide. In some embodiments, the Group IA metal hydroxide is chosen from NaOH, KOH, and LiOH. In some embodiments, the Group IA metal hydroxide is NaOH.

In some embodiments, the reaction of the compound of formula (III) or a salt thereof with a metal hydroxide or other suitable base is conducted in the presence of at least one solvent. In some embodiments, the at least one solvent is a mixture of two or more solvents. In some embodiments, the at least one solvent is a mixture of water and a $C_1$-$C_3$ alcohol. In some embodiments, the $C_1$-$C_3$ alcohol is methanol ($CH_3OH$).

In some embodiments, the reaction of the compound of formula (III) or a salt thereof with a metal hydroxide or other suitable base is conducted at a temperature of at most about 5° C. In some embodiments, the reaction of the compound of formula (III) or a salt thereof with a metal hydroxide or other suitable base is conducted at a temperature of from about −10° C. to about 5° C. In some embodiments, the reaction of the compound of formula (III) or a salt thereof with a metal hydroxide or other suitable base is conducted at a temperature of from about −5° C. to about 5° C. In some embodiments, the reaction of the compound of formula (III) or a salt thereof with a metal hydroxide or other suitable base is conducted at a temperature of from about −5° C. to about 1° C.

In some embodiments, the reaction of the compound of formula (III) or a salt thereof with a metal hydroxide or other suitable base further comprises acidifying the reaction mixture. In some embodiments, the reaction mixture is acidified with dilute hydrochloric acid. In some embodiments, the product is extracted with ethyl acetate, and crystallized from acetone and heptane. In some embodiments, the crystallization can remove stereoisomeric impurities (e.g., a small amount of cis-isomer when the trans isomer is desired). In some embodiments, the chemical yield for the process is from about 80-90%.

Also provided is a method for preparing a compound of formula (I) or a

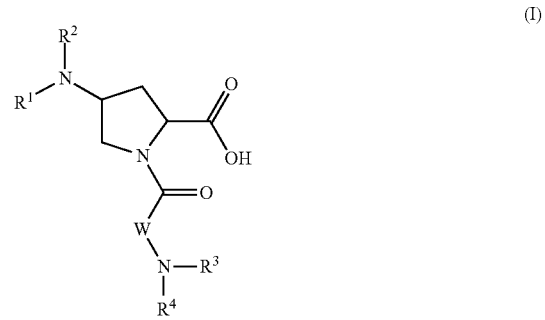

wherein:
one of $R^1$ and $R^2$ is hydrogen or $C_1$-$C_6$ alkyl, and the other is —$C(O)R^5$;
wherein $R^5$ is chosen from:
optionally substituted $C_6$-$C_{10}$ aryl;
optionally substituted heteroaryl including 5-10 atoms;
optionally substituted $C_1$-$C_{20}$ alkyl;
optionally substituted $C_1$-$C_{20}$ haloalkyl;
optionally substituted $C_7$-$C_{12}$ aralkyl;
optionally substituted heteroaralkyl including 6-12 atoms;
optionally substituted $C_3$-$C_{10}$ cycloalkyl; and
optionally substituted $C_3$-$C_{10}$ cycloalkenyl;
W is $C_{1-6}$ alkylene; and
$R^3$ and $R^4$ may be the same or different, and are each independently chosen from hydrogen, optionally substituted $C_1$-$C_6$ alkyl, —$C(O)OR^6$, and —$C(O)R^9$;
wherein $R^6$ is optionally substituted $C_1$-$C_{20}$ alkyl; and
wherein $R^9$ is chosen from
hydrogen;
optionally substituted $C_6$-$C_{10}$ aryl;
optionally substituted heteroaryl including 5-10 atoms;
optionally substituted $C_1$-$C_{20}$ alkyl;
optionally substituted $C_3$-$C_{10}$ cycloalkyl; and
optionally substituted heterocycloalkyl including 5-10 atoms;
the method comprising:
reacting a compound of formula (III) or a salt thereof

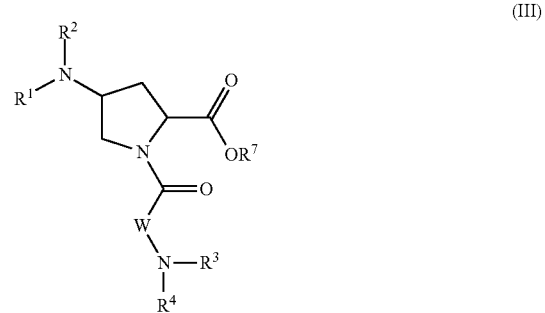

wherein $R^7$ is chosen from hydrogen and optionally substituted $C_1$-$C_6$ alkyl; with a metal hydroxide or other suitable base to provide a compound of formula (I) or a salt thereof.

In some embodiments, the method further comprises converting the compound of formula (II) or a salt thereof to a compound of formula (III) or a salt thereof by contacting the compound of formula (II) or a salt thereof with a compound of formula (IV):

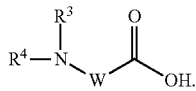
(IV)

In some embodiments, the compound of formula (IV) is glycine (e.g., $R^3$ and $R^4$ are H and W is —$CH_2$—). In some embodiments, the compound of formula (IV) is Boc-Gly-OH (e.g., one of $R^3$ and $R^4$ is H and the other is tert-butyloxy carbonyl, and W is —$CH_2$—). In some embodiments, the compound of formula (IV) is CHO-Gly-OH (e.g., one of $R^3$ and $R^4$ is H and the other is CHO (formyl), and W is —$CH_2$—).

In some embodiments, W in formula (IV) is —$CH_2$—; and one of $R^3$ and $R^4$ in formula (IV) is hydrogen and the other is —$C(O)OR^6$. In some embodiments, $R^6$ in formula (IV) is $C_1$-$C_6$ alkyl (e.g., tert-butyl).

In some embodiments, the compound of formula (II) or a salt thereof is contacted with the carboxylic acid of formula (IV) in the presence of a coupling agent. The term "coupling agent" refers to a compound used when coupling together an amine and a carboxylic acid. In some embodiments, the coupling agent is a carbodiimide. In some embodiments, the coupling agent is N-(3-dimethylaminopropyl)-N'-ethylcarbodiimide hydrochloride (EDAC) or dicyclohexylcarbodiimide (DCC).

In some embodiments, the compound of formula (II) or a salt thereof is contacted with the carboxylic acid of formula (IV) in the presence of a coupling agent and a hydroxylated moiety. In some embodiments, the hydroxylated moiety is N-hydroxybenzotriazole (HOBt), 1-hydroxy-7-azabenzotriazole (HOAt), or pentafluorophenol.

In some embodiments, the carboxylic acid of formula (IV) is converted to a mixed anhydride. In some embodiments, the compound of formula (IV) is Boc-Gly-OH and the mixed anhydride is formed by treatment of the compound of formula (IV) with ethyl chloroformate, optionally in the presence of triethylamine, followed by reaction with a compound of formula (II).

In some embodiments, the compound of formula (III) or a salt thereof is isolated from acetone as an acetone solvate, which may eliminate the need for concentrating the reaction mixture to dryness.

In some embodiments, the yield is greater than 70%, such as greater than 80%, for example, greater than 85%, such as about 86%.

In some embodiments, $R^3$ is chosen from hydrogen and optionally substituted $C_1$-$C_6$ alkyl when $R^4$ is —$C(O)OR^6$. Thus, in some embodiments, the reaction of the compound of formula (III) or a salt thereof with a metal hydroxide or other suitable base, may provide a compound of formula (I-A) or a salt thereof:

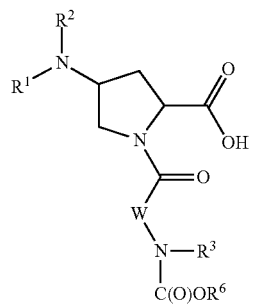
(I-A)

wherein $R^3$ is chosen from hydrogen and optionally substituted $C_1$-$C_6$ alkyl.

In some embodiments, $R^3$ in formula (I-A) is hydrogen, and $R^6$ in formula (I-A) is tert-butyl. In some embodiments, $R^3$ in formula (I-A) is hydrogen, and $R^6$ in formula (I-A) is benzyl.

In some embodiments, W in formula (I-A) is —$CH_2$—. In some embodiments, $R^5$ in formula (I-A) is phenyl.

In some embodiments, the reaction of the compound of formula (III) with a metal hydroxide or other suitable base provides a compound of formula (I-A-1) or a salt thereof:

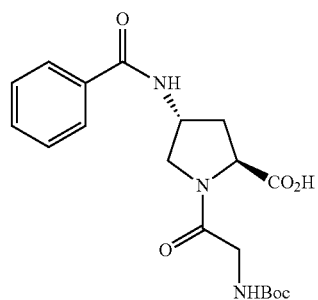
(I-A-1)

In some embodiments, the methods further include removing the —$C(O)OR^6$ group of the compound of formula (I-A) (i.e., deprotecting the nitrogen atom to which $R^3$ and $R^4$ are attached) to provide a compound of formula (I-B) or a salt thereof:

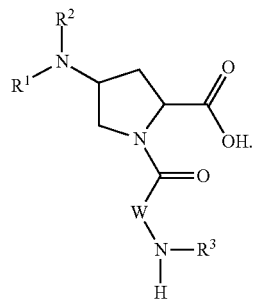
(I-B)

In some embodiments, the method further comprises converting the compound of formula (I-A) or a salt thereof to a compound of formula (I-B) or a salt thereof. In some embodiments, converting the compound of formula (I-A) or a salt thereof to a compound of formula (I-B) or a salt thereof comprises contacting the compound of formula (I-A) with at least one acid.

In some embodiments, the at least one acid is HCl, e.g., anhydrous HCl or concentrated aqueous hydrochloric acid.

In some embodiments, a solvent is used for the conversion. In some embodiments, the solvent is an organic solvent, such as dioxane or acetone. In some embodiments, the solvent is water.

In some embodiments, $R^3$ in formula (I-A) is hydrogen, and $R^6$ in formula (I-A) is tert-butyl.

In some embodiments, converting the compound of formula (I-B) or a salt thereof to a compound of formula (I-B) or a salt thereof comprises subjecting the compound of formula (I-A) to catalytic hydrogenation. In some embodiments, $R^3$ in formula (I-A) is hydrogen, and $R^6$ in formula (I-A) is benzyl.

In some embodiments, subjecting the compound of formula (I-A) to catalytic hydrogenation comprises contacting the compound of formula (I-A) with $H_2$ gas and a transition metal catalyst. In some embodiments, the transition metal catalyst is palladium. In some embodiments, subjecting the compound of formula (I-A) to transfer hydrogenation comprises contacting the compound of formula (I-A) with cyclohexene and a transition metal catalyst. In some embodiments, the transition metal catalyst is palladium.

In some embodiments, the compound of formula (I-B) is obtained as the free acid. In some embodiments, the compound of formula (I-B) is obtained as a salt (e.g., as an HCl salt).

In some embodiments, the method further comprises converting the compound of formula (I-A-1) or a salt thereof to a compound of formula (I-B-1) or a salt thereof:

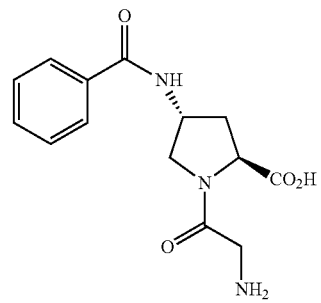

(I-B-1)

In some embodiments, subsequent deprotection of (2S,4R)-4-benzamido-1-(2-(tert-butoxycarbonylamino)acetyl)pyrrolidine-2-carboxylic acid to (2S,4R)-1-(2-aminoacetyl)-4-benzamidopyrrolidine-2-carboxylic acid, hydrochloride is accomplished by treating the former compound with concentrated hydrochloric acid in acetone. The precipitated product is dissolved by addition of water to form a clear solution, which is filtered to remove particulates. The desired product is then crystallized by the addition of acetone. In some embodiments, the crystalline hydrochloride is isolated as a monohydrate. The chemical yield for the process can be about 80-95%.

An exemplary, but non-limiting example is outlined in Scheme 1 below. As shown, compound v (i.e., a compound of formula (I)) is obtained by reacting compound iii (i.e., a compound of formula (II)) with a formylated glycine compound to give a compound iv, which is subsequently reacted with a base.

Scheme 1

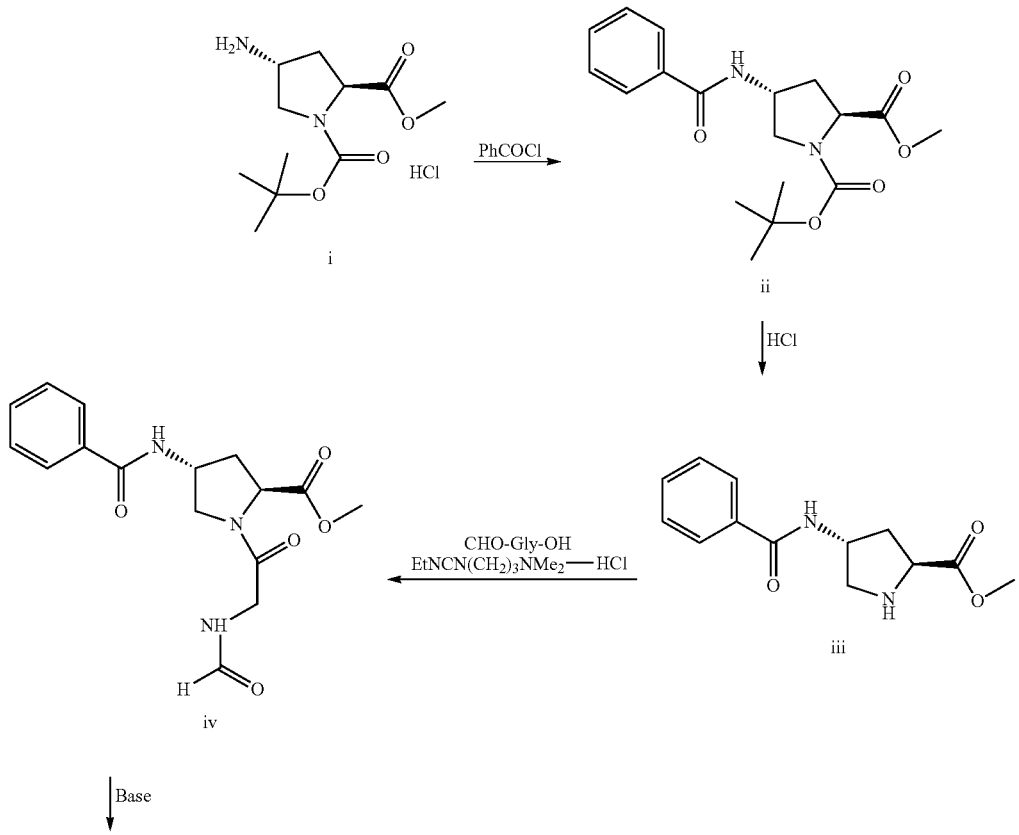

-continued

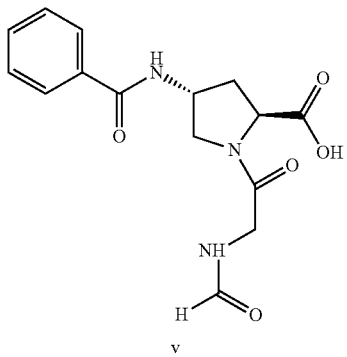

v

The base used to convert compound iv into compound v can be a metal hydroxide (e.g., LiOH, NaOH, KOH). Alternatively, the base can be a metal carbonate (e.g., $Li_2CO_3$, $Na_2CO_3$, $K_2CO_3$) or metal hydrogencarbonate (e.g., $NaHCO_3$, $KHCO_3$) in combination with water.

In some embodiments, the compound of formula (II) is prepared from a compound of formula (V). In some embodiments, the compound of formula (V) is prepared from a compound of formula (VIII) or a compound of formula (X). The method for preparing a compound of formula (I) from a compound of formula (II) can further include one or both of those methods.

In some embodiments, the compound of formula (II) is prepared by a method comprising:

contacting a compound of formula (V):

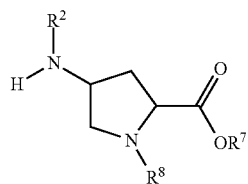

(V)

wherein:
$R^2$ is chosen from hydrogen and optionally substituted $C_1$-$C_6$ alkyl;
$R^7$ is chosen from hydrogen and optionally substituted $C_1$-$C_6$ alkyl; and
$R^8$ is a nitrogen protecting group;

with an activated carboxylic acid to provide a compound of formula (VII) or a salt thereof:

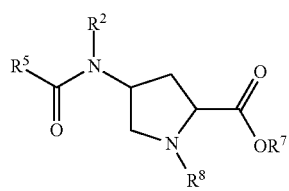

(VII)

and
removing the nitrogen protecting group $R^8$ from the compound of formula (VII).

The foregoing method for preparing a compound of formula (II) from a compound of formula (V) can be practiced separately from, or in conjunction with, the methods described herein for preparing a compound of formula (I) from a compound of formula (II) or a compound of formula (III).

In some embodiments, $R^2$ in formulae (V) and (VII) is hydrogen.

In some embodiments, $R^8$ in formulae (V) and (VII) is —C(O)O$R^a$, in which $R^a$ is chosen from:
optionally substituted $C_6$-$C_{10}$ aryl;
optionally substituted heteroaryl including 5-10 atoms;
optionally substituted $C_1$-$C_{20}$ alkyl;
optionally substituted $C_1$-$C_{20}$ haloalkyl;
optionally substituted $C_7$-$C_{12}$ aralkyl;
optionally substituted heteroaralkyl including 6-12 atoms;
optionally substituted $C_3$-$C_{10}$ cycloalkyl; and
optionally substituted $C_3$-$C_{10}$ cycloalkenyl;

In some embodiments, $R^8$ in formulae (V) and (VII) is —C(O)O(tert-butyl) or —C(O)O(benzyl).

In some embodiments, $R^5$ in formula (VII) is optionally substituted $C_6$-$C_{10}$ aryl or optionally substituted heteroaryl including 5-10 atoms. In some embodiments, $R^5$ is optionally substituted $C_6$-$C_{10}$ aryl. In some embodiments, $R^5$ is phenyl.

In some embodiments, $R^8$ in formulae (V) and (VII) is an acid labile nitrogen protecting group and removing the protecting group from the compound of formula (VII) comprises contacting the compound of formula (VII) with at least one acid. In some embodiments, the at least one acid is HCl or trifluoroacetic acid. In some embodiments, the nitrogen protecting group is —C(O)O(tert-butyl).

In some embodiments, $R^8$ in formulae (V) and (VII) is a nitrogen protecting group that is susceptible to cleavage by hydrogenolysis and removing the protecting group from the compound of formula (VII) comprises subjecting the compound of formula (VII) to catalytic hydrogenation. In some embodiments, the nitrogen protecting group is —C(O)O(benzyl).

In some embodiments, subjecting the compound of formula (VII) to catalytic hydrogenation comprises contacting the compound of formula (VII) with $H_2$ gas and a transition metal catalyst. In some embodiments, the transition metal catalyst is palladium.

In some embodiments, $R^8$ in formulae (V) and (VII) is a nitrogen protecting group that is susceptible to cleavage by hydrogenolysis and removing the protecting group from the compound of formula (VII) comprises subjecting the compound of formula (VII) to transfer hydrogenation. In some embodiments, subjecting the compound of formula (VII) to transfer hydrogenation comprises contacting the compound of formula (VII) with cyclohexene and a transition metal catalyst. In some embodiments, the transition metal catalyst is palladium.

In some embodiments, the activated carboxylic acid is a compound of formula (VI):

$$R^5C(O)Cl \qquad (VI).$$

In some embodiments, removing the protecting group from the compound of formula (VII) provides the compound of formula (II) as an HCl salt.

In some embodiments, benzoylation of commercially available N-Boc-trans-4-amino-L-proline methyl ester (HCl salt or free base) is accomplished using conventional amide bond forming methods, including reacting with benzoic acid in the presence of a coupling agent, reacting with corresponding anhydride of benzoic acid (or mixed anhydride), or with benzoyl halide. In some embodiments, N-Boc-trans-4-amino-L-proline methyl ester (either as a HCl salt or free base) is treated with benzoyl chloride under Schotten-Bauman conditions, i.e., in a biphasic mixture of organic solvent (e.g., ethyl acetate (EtOAc), toluene, methyl tert-butyl ether (MTBE), etc.) and water in the presence of a base (e.g., NaHCO₃). For example, Schotten-Bauman conditions can include EtOAc, water, and NaHCO₃. In some embodiments, azeotropic distillation can be used to dry the reaction mixture when toluene is employed as the organic solvent (the use of toluene can also facilitate the isolation of the formula (II) compound as a crystalline solid after deprotection).

In some embodiments, benzoylation is performed by treatment with benzoyl halide (e.g., benzoyl chloride) in an organic solvent (e.g., CH₂Cl₂) in the presence of organic (e.g., pyridine) or inorganic base.

In some embodiments, deprotection of the formula (VII) compound is carried out using an acid (e.g., HCl, CF₃COOH, etc.) in an ethereal solvent (Et₂O, dioxane, etc.). In some embodiments, deprotection of the formula (VII) compound is carried out using anhydrous HCl in MeOH. The use of anhydrous HCl in MeOH can minimize the likelihood of unwanted hydrolysis side reactions. In some embodiments, the compound of formula (VII) is not isolated prior to deprotection.

In some embodiments, the compound of formula (II) is prepared by a method comprising:
contacting a compound of formula (V-1):

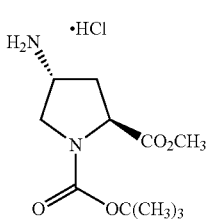

(V-1)

with benzoyl chloride to provide a compound of formula (VII-1):

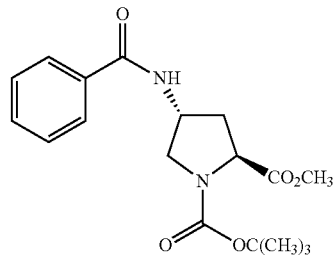

(VII-1)

and
removing —C(O)O(tert-butyl) from the compound of formula (VII-1).

In some embodiments, a compound of formula (V), in which $R^2$ is hydrogen, is prepared by a method comprising
contacting a compound of formula (VIII):

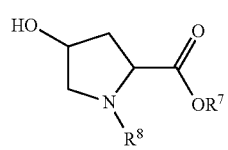

(VIII)

wherein $R^7$ is chosen from hydrogen and optionally substituted $C_1$-$C_6$ alkyl, with a compound of the formula $(R^b)(R^c)$NH, wherein $R^b$ and/or $R^c$ are other than hydrogen to provide a compound of formula (IX):

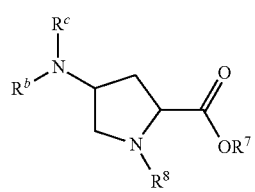

(IX)

and
(ii) converting the compound of formula (IX) to a compound of formula (V), in which $R^2$ is hydrogen.

In some embodiments, the compound of the formula $(R^b)(R^c)$NH is chosen such that when it is incorporated into a substrate it can be transformed in one or more chemical steps into an amino group (i.e., —NH₂). In some embodiments, the compound of the formula $(R^b)(R^c)$NH is chosen from phthalimide, O-tert-butyl carbamate, N-Boc ethyl oxamate, benzhydryl amine, trityl amine, lithium hexamethyldisilazane, triphenylsilyl amine, LiNH₂, allylamine, and bis(allyl)amine.

In some embodiments, the methods of preparing compounds of Formula (V) involve the conversion of a trans-4-hydroxy-L-proline (or derivative thereof) to a trans-4-amino-L-proline (or derivative thereof). An exemplary, but non-limiting example is discussed below and outlined in Scheme 2.

Scheme 2

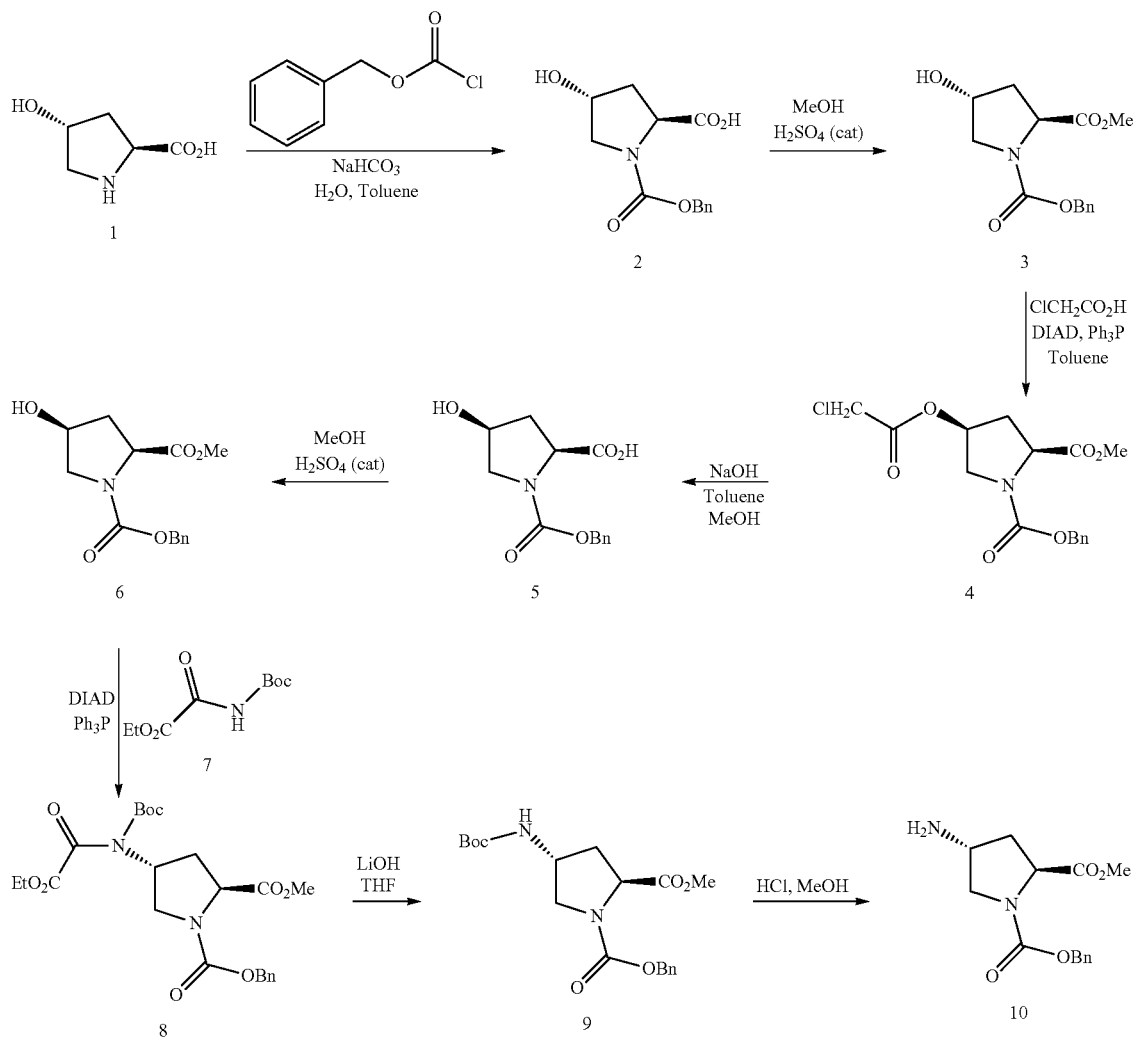

Commercially available trans-4-hydroxy-L-proline 1 can be converted to 1-benzyl 2-methyl (2S,4R)-4-Hydroxypyrrolidine-1,2-dicarboxylate 3 based on literature references (Bridges et al. *J. Med. Chem.* 1991, 34, 717; Gregson et al. *J. Med. Chem.* 2004, 47, 1161).

Compound 3 can be treated with a water soluble organic acid such as chloroacetic acid (Hughes and Reamer, J. Org. Chem., 1996, 61, 2967) in presence of triphenylphosphine and an azodicarboxylate such as diisopropyl azodicarboxylate (DIAD) in a solvent such as toluene to afford compound 4. An advantage associated with chloroacetic acid and the like is that the acid can be removed from the reaction product upon washing. The ester 4 can be saponified in situ by addition of an alcohol such as methanol as co-solvent and an aqueous base solution such as aqueous sodium hydroxide. After saponification, the by-products from the Mitsunobu reaction, i.e., triphenylphosphine oxide and the hydrazide byproduct, can be removed by extraction of the basic solution with a solvent such as toluene, thus reducing the likelihood that chromatographic separation would be needed to remove the by-products and thus rendering the new process amenable to scale up. Neutralization and back-extraction with an organic solvent such as dichloromethane affords acid 5.

The resulting acid 5 can be esterified under conventional acid catalyzed esterification conditions with acid such as sulfuric acid in an alkyl alcohol such as MeOH to furnish cis-4-hydroxy-L-proline methyl ester 6.

The cis-4-hydroxy-proline derivative 6 can be coupled with N-Boc-ethyl oxamate (7) (see Berree et al. Tetrahedron Lett., 1998, 39, 8275) under conventional Mitsunobu reaction conditions using triphenyl phosphine and DIAD to provide the protected trans-4-aminoproline derivative 8. Oxamate 8 can be selectively hydrolyzed with aqueous lithium hydroxide, and the Boc protecting group can be subsequently cleaved with hydrochloric acid in methanol. At this point, the desired product 10 remains in the acidic aqueous phase. The byproducts from the Mitsunobu reaction can be removed by extraction with an organic solvent such as toluene. The acidic aqueous phase is then neutralized and extracted with another organic solvent such as ethyl acetate to give N-Cbz protected trans-4-amino-L-proline methyl ester 10, therefore, chromatographic separation can again be avoided in this portion of the process.

In some embodiments, the methods involve the conversion of a cis-4-hydroxy-L-proline (or derivative thereof) to a trans- 4-amino-L-proline (or derivative thereof). An exemplary, but non-limiting example is discussed below and outlined in Scheme 3.

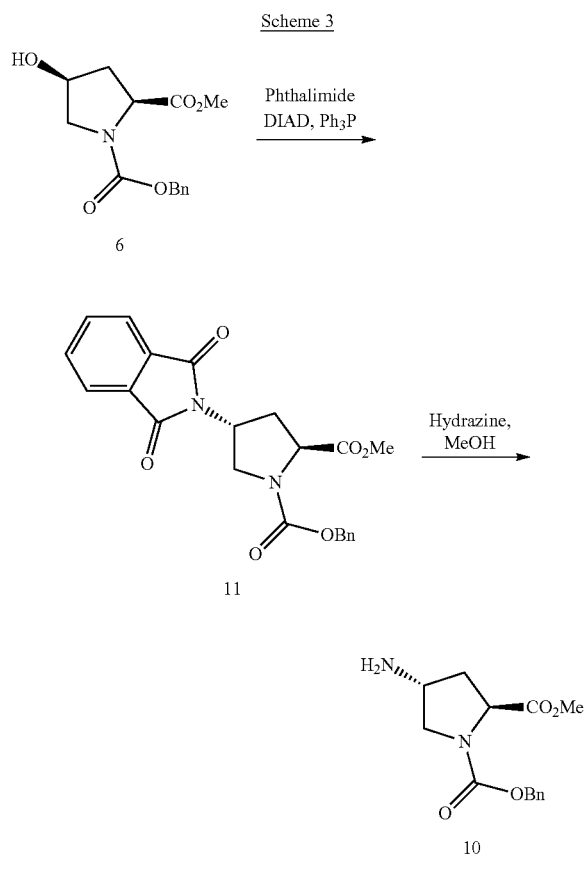

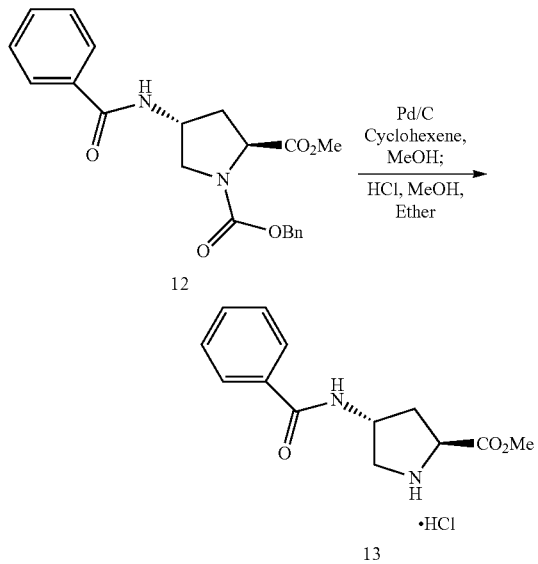

The alcohol 6 can be reacted with phthalimide in the presence of triphenylphosphine and diisopropyl azodicarboxylate in solvents such as tetrahydrofuran and toluene to give compound 11, which can be isolated as a crude toluene solution. The crude phthalimide 11 can then be converted to amine 10 by the treatment with hydrazine hydrate in methanol. The amine can be isolated in high purity through an extractive work-up under acidic conditions. The extractive workup under acidic conditions in this case allows of the by-products of the Mitsunobu reaction such as triphenylphosphine oxide, to be removed without the use of chromatography. The overall yield for this process can be about 66%.

In some embodiments, the amine 10 can be used to prepare compounds of formula (II), such as compound 13 via a compound of formula (VII), such as compound 12. See Scheme 4.

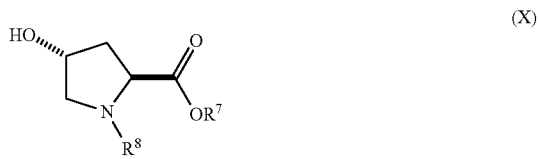

In some embodiments, a stereoisomer or an enriched stereoisomeric mixture of a compound of formula (V) is used, wherein said stereoisomer or enriched stereoisomeric mixture of a compound of formula (V) is prepared by a method comprising:

contacting a compound of formula (X)

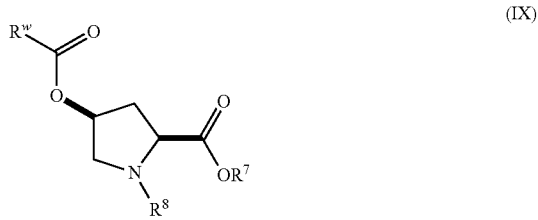

wherein $R^7$ is chosen from hydrogen and optionally substituted $C_1$-$C_6$ alkyl; and $R^8$ is hydrogen or a nitrogen protecting group with a compound of formula $R^wCO_2H$ (wherein $R^w$ is lower alkyl or lower haloalkyl), a compound of formula $P(R^d)_3$ (wherein $R^d$ at each occurrence is, independently, optionally substituted $C_6$-$C_{10}$ aryl or optionally substituted heteroaryl including 5-10 atoms), and a di($C_1$-$C_6$ alkyl)azodicarboxylate to provide a compound of formula (XI):

(IX)

contacting the compound of formula (XI) with a metal hydroxide to provide a compound of formula (XII) or a salt thereof:

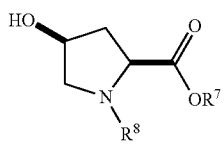

(XII)

contacting the compound of formula (XII) with a compound of formula (R$^b$)(R$^c$)NH (in which R$^b$ and/or R$^c$ are other than hydrogen) to provide a compound of formula (XIII):

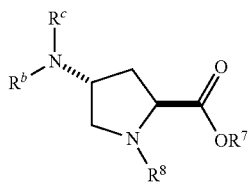

(XIII)

and
converting the compound of formula (XIII) to a compound of formula (V), in which R$^2$ in formula (V) is hydrogen.

For purposes of clarification, the stereochemistry depicted in formula (X) and in each of the formulas is intended to show relative stereochemistry. However, it is understood that the aforementioned stereoselective or stereospecific methods described herein can be used to prepare any one of the four possible stereoisomeric products (i.e., 2S,4R; 2R, 4S; 2S,4S, and 2R, 4R).

In some embodiments, R$^8$ is C(O)OR$^a$ wherein R$^a$ is chosen from optionally substituted C$_6$-C$_{10}$ aryl; optionally substituted heteroaryl including 5-10 atoms; optionally substituted C$_1$-C$_{20}$ alkyl; optionally substituted C$_1$-C$_{20}$ haloalkyl; optionally substituted C$_7$-C$_{12}$ aralkyl; optionally substituted heteroaralkyl including 6-12 atoms; optionally substituted C$_3$-C$_{10}$ cycloalkyl; and optionally substituted C$_3$-C$_{10}$ cycloalkenyl.

In some embodiments, R$^8$ is —C(O)O(tert-butyl) or —C(O)O(benzyl). In some embodiments, R$^8$ is —C(O)O(benzyl).

In some embodiments, the compound of formula P(R$^d$)$_3$ is triphenylphosphine.

In some embodiments, the di(C$_1$-C$_6$ alkyl)azodicarboxylate is diisopropyl azodicarboxylate.

In some embodiments, other phosphines and di(C$_1$-C$_6$ alkyl)azodicarboxylates that are suitable for use in a Mitsunobu reaction are employed.

In some embodiments, the method can be carried out and scaled up without the use of purification by chromatography. In some embodiments, the post-Mitsunobu reaction products can be purified by non-chromatographic methods, e.g., extraction, and be substantially free of Mitsunobu reaction by-products.

The foregoing methods for preparing a compound of formula (V) from a compound of formula (VIII) or (X) (as well as variants thereof) can be practiced separately from, or in conjunction with, the methods described herein for preparing a compound of formula (II) from a compound of formula (V), which in turn can be practiced separately from, or in conjunction with, the methods described herein for preparing a compound of formula (I) from a compound of formula (II).

In some embodiments, the compound of formula (I) or a salt thereof is:

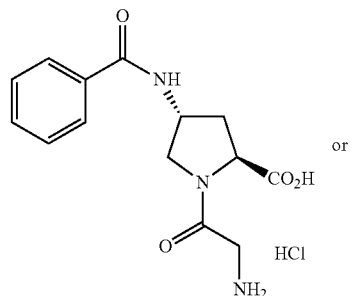

In some embodiments, the compound of formula (II) or a salt thereof is:

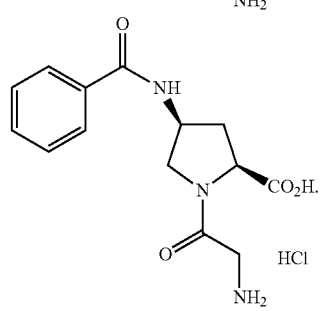

In some embodiments, the compound of formula (III) or a salt thereof is:

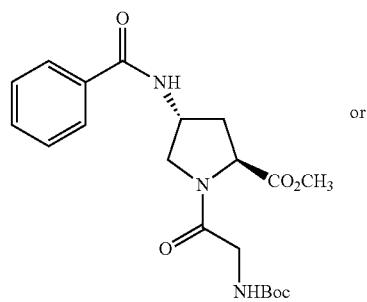

-continued

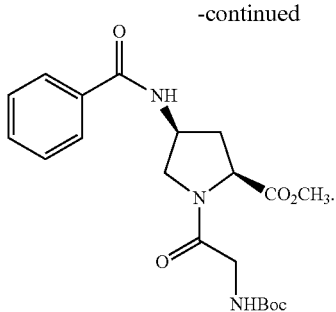

In some embodiments, the compound of formula (IV) or a salt thereof is Boc-Gly-OH.

Also provided is a composition comprising
(1) a compound of formula (I) or a salt thereof

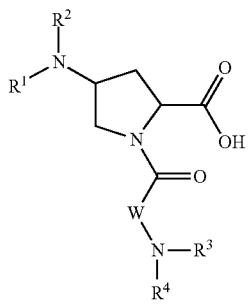

(I)

and/or
a compound of formula (III) or a salt thereof

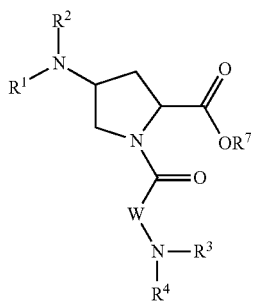

(III)

wherein
one of $R^1$ and $R^2$ is hydrogen or $C_1$-$C_6$ alkyl, and the other is —C(O)$R^5$;
wherein $R^5$ is chosen from:
optionally substituted $C_6$-$C_{10}$ aryl;
optionally substituted heteroaryl including 5-10 atoms;
optionally substituted $C_1$-$C_{20}$ alkyl;
optionally substituted $C_1$-$C_{20}$ haloalkyl;
optionally substituted $C_7$-$C_{12}$ aralkyl;
optionally substituted heteroaralkyl including 6-12 atoms;
optionally substituted $C_3$-$C_{10}$ cycloalkyl; and
optionally substituted $C_3$-$C_{10}$ cycloalkenyl;
W is $C_{1-6}$ alkylene;
$R^3$ and $R^4$ may be the same or different and are each independently chosen from hydrogen, optionally substituted $C_1$-$C_6$ alkyl, —C(O)O$R^6$, and —C(O)$R^9$;

wherein $R^6$ is optionally substituted $C_1$-$C_{20}$ alkyl; and
wherein $R^9$ is chosen from
hydrogen;
optionally substituted $C_6$-$C_{10}$ aryl;
optionally substituted heteroaryl including 5-10 atoms;
optionally substituted $C_1$-$C_{20}$ alkyl;
optionally substituted $C_3$-$C_{10}$ cycloalkyl; and
optionally substituted heterocycloalkyl including 5-10 atoms; and
$R^7$ is chosen from hydrogen and optionally substituted $C_1$-$C_6$ alkyl; and
(2) a detectable amount of one or more compounds selected from:
N-((7R,8aS)-1,4-dioxooctahydropyrrolo[1,2-a]pyrazin-7-yl)benzamide or a salt thereof, i.e., a compound of formula

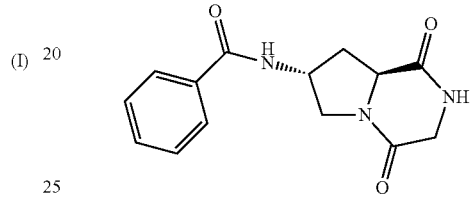

or a salt thereof;
triphenylphosphine;
triphenylphosphine oxide;
a hydrazine dicarboxylate;
triethylamine;
benzotriazole;
(2S,4R)-4-benzamido-1-(2-(tert-butylamino)acetyl)pyrrolidine-2-carboxylic acid or a salt thereof, i.e., a compound of formula:

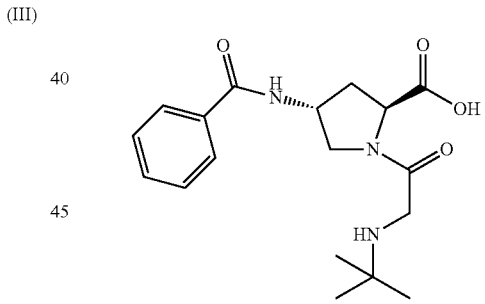

or a salt thereof;
and a compound of formula (II) or a salt thereof:

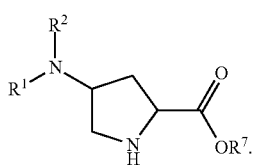

(II)

In some embodiments, the composition comprises greater than about 95%, such as greater than about 98%, for example, greater than about 99% of a compound of formula (I). In some embodiments, the composition comprises greater than about 99.9% of a compound of formula (I).

In some embodiments, the compound of formula (I) is (2S,4R)-1-(2-aminoacetyl)-4-benzamidopyrrolidine-2-carboxylic acid or a salt thereof. In some embodiments, the compound of formula (I) is (2S,4R)-1-(2-aminoacetyl)-4-benzamidopyrrolidine-2-carboxylic acid hydrochloride. In some embodiments, the compound of formula (I) is (2S,4R)-1-(2-aminoacetyl)-4-benzamidopyrrolidine-2-carboxylic acid hydrochloride monohydrate. In some embodiments, the compound of formula (I) is (2S,4R)-4-benzamido-1-(2-(tert-butoxycarbonylamino)acetyl)pyrrolidine-2-carboxylic acid. In some embodiments, the compound of formula (III) is (2S,4R)-methyl 1-(2-aminoacetyl)-4-benzamidopyrrolidine-2-carboxylate. In some embodiments, the compound of formula (III) is (2S,4R)-methyl 4-benzamido-1-(2-(tert-butoxycarbonylamino)acetyl)pyrrolidine-2-carboxylate.

Also provided is (2S,4R)-1-(2-aminoacetyl)-4-benzamidopyrrolidine-2-carboxylic acid hydrochloride monohydrate. The compound (2S,4R)-1-(2-aminoacetyl)-4-benzamidopyrrolidine-2-carboxylic acid may be prepared according to methods known in the art (e.g., as described in U.S. patent application Ser. No. 11/643,192, which is incorporated herein by reference in its entirety) and as described herein.

Also provided is a method for preparing crystalline (2S,4R)-1-(2-aminoacetyl)-4-benzamidopyrrolidine-2-carboxylic acid hydrochloride monohydrate. Such preparation method includes the steps of providing a solution of (2S,4R)-1-(2-aminoacetyl)-4-benzamidopyrrolidine-2-carboxylic acid hydrochloride in a crystallization medium wherein the crystallization medium comprises water and one or more water-miscible organic solvents. Such preparation method further includes maintaining the solution for a time and under conditions suitable for forming (2S,4R)-1-(2-aminoacetyl)-4-benzamidopyrrolidine-2-carboxylic acid hydrochloride monohydrate.

In some embodiments, the (2S,4R)-1-(2-aminoacetyl)-4-benzamidopyrrolidine-2-carboxylic acid hydrochloride is added, e.g., portionwise, as a solid to the crystallization medium. In some embodiments, the crystallization medium is heated to an elevated temperature, e.g., at reflux.

In some embodiments, the (2S,4R)-1-(2-aminoacetyl)-4-benzamidopyrrolidine-2-carboxylic acid hydrochloride is added, e.g., portionwise, as a solid to one or more water-miscible organic solvents. In some embodiments, the one or more water-miscible organic solvents is heated to an elevated temperature, e.g., at reflux. The solution of the (2S,4R)-1-(2-aminoacetyl)-4-benzamidopyrrolidine-2-carboxylic acid hydrochloride in the one or more water-miscible organic solvents is then combined with water and any other water-miscible organic solvents which are found in the crystallization medium.

In some embodiments, the solution provided is a fully dissolved solution of (2S,4R)-1-(2-aminoacetyl)-4-benzamidopyrrolidine-2-carboxylic acid hydrochloride. In some embodiments, the solution provided is a partially dissolved suspension or slurry of (2S,4R)-1-(2-aminoacetyl)-4-benzamidopyrrolidine-2-carboxylic acid hydrochloride.

The solubility of the (2S,4R)-1-(2-aminoacetyl)-4-benzamidopyrrolidine-2-carboxylic acid hydrochloride will vary depending on the composition of the medium, as is well-appreciated in the art, but, in some embodiments, is at least about 1 mg/mL, such as from about 1 to about 500 mg/mL, for example, from about 5 to about 100 mg/mL.

In some embodiments, the water-miscible organic solvent is selected from alcohols, ketones, ethers, or a combination of such solvents. In some embodiments, the water-miscible organic solvent is selected from $C_{1-4}$ alcohols, $C_{1-6}$ ketones, and $C_{1-6}$ ethers. Where more than one water-miscible organic solvent is used, a solvent of the same type or different type may be combined. For example, if an alcohol is selected, another alcohol may also be selected for use in the solvent mixture.

Suitable alcohols include methanol, ethanol, n-propanol, isopropanol, t-butanol, and the like. Suitable ketones include acetone, diethyl ketone, and the like. Suitable ethers include t-butyl methyl ether, diethyl ether, 1,3-dioxane, 1,4-dioxane, tetrahydrofuran, ethylene glycol dimethyl ether, and the like. In some embodiments, the alcohol is isopropanol, the ketone is acetone, and the ether is t-butyl methyl ether.

The choice of water-miscible organic solvent or combination of water-miscible organic solvents is well within the ability of one skilled in the art, and will depend on factors such the desired scale, yield, operating temperature, time of operation, and the like. For combinations of water-miscible organic solvents, the ratio of the components may be varied. For example, the ratio of alcohol to ketone may range from a ratio of about 1:9 to about 9:1. Ratios outside this range are also contemplated. Ternary combinations of an alcohol, ketone, and ether are also provided. The ratio of three components may vary without limit. In one embodiment, a combination comprising up to about 10% of an alcohol, up to about 5% of an ether, and at least about 85% of a ketone is used.

Water is included in the crystallization medium. Water may be adventitiously present, but in some embodiments water is combined with the water-miscible organic solvent. The amount of water in the solvent mixture is generally no more than 25% by volume. The solution can comprise less than 10% water by volume, and in some embodiments the water is less than 5% by volume. In some embodiments, the water-miscible organic solvent portion is about 97.5% by volume and water is about 2.5% by volume.

With respect to conditions suitable for forming (2S,4R)-1-(2-aminoacetyl)-4-benzamidopyrrolidine-2-carboxylic acid hydrochloride monohydrate, any method known in the art may be used, such as cooling the solution, adding seeding crystals, reducing the volume of the solvent under ambient or reduced pressure, adding an anti-solvent, using diffusion techniques, and/or by combination of these techniques. The solution may left undisturbed, or stirred during the crystallization process. In some embodiments, the solution is maintained at room temperature and stirred until the crystallization is sufficiently complete. In some embodiments, the solution is maintained at room temperature and at least some of the crystallization medium is permitted to evaporate, whereupon crystals form. The evaporation process may be carried out at ambient pressure or under reduced pressure, and may be with or without control of the temperature of the medium.

In some embodiments, the method further includes the step of recovering the (2S,4R)-1-(2-aminoacetyl)-4-benzamidopyrrolidine-2-carboxylic acid hydrochloride monohydrate, which may be accomplished by means known by those of skill in the art, such as filtration, centrifugation, decanting, and the like. In some embodiments, the method further comprises washing the recovered (2S,4R)-1-(2-aminoacetyl)-4-benzamidopyrrolidine-2-carboxylic acid hydrochloride monohydrate with a suitable solvent upon recovery of the (2S,4R)-1-(2-aminoacetyl)-4-benzamidopyrrolidine-2-carboxylic acid hydrochloride monohydrate. In some embodiments, the method further comprises drying the (2S,4R)-1-(2-aminoacetyl)-4-benzamidopyrrolidine-2-carboxylic acid hydrochloride monohydrate. Drying may be performed at ambient or reduced pressure, and at ambient or elevated temperature. For example, a vacuum drying oven may be used. In some embodiments, the (2S,4R)-1-(2-aminoacetyl)-4-benzamidopyrrolidine-2-carboxylic acid hydrochloride monohydrate is dried at about 45° C. under vacuum.

In some embodiments, the crystalline (2S,4R)-1-(2-aminoacetyl)-4-benzamidopyrrolidine-2-carboxylic acid hydrochloride monohydrate is characterized by X-ray powder diffraction.

There are a number of analytical methods one of ordinary skill in the art in solid-state chemistry can use to analyze solid forms. The term "analyze" as used herein means to obtain information about the solid-state structure of solid forms. For example, X-ray powder diffraction is a suitable technique for differentiating amorphous solid forms from crystalline solid forms and for characterizing and identifying crystalline solid forms of a compound. X-ray powder diffraction is also suitable for quantifying the amount of a crystalline solid form (or forms) in a mixture.

The term "characterize" as used herein means to select an appropriate set of data capable of distinguishing one solid form from another. That set of data in X-ray powder diffraction is the position of one or more peaks. Selecting which X-ray powder diffraction peaks define a particular form is said to characterize that form.

When characterizing and/or identifying crystalline solid forms of the same chemical compound with X-ray powder diffraction, it is often not necessary to use the entire powder pattern. A smaller subset of the entire powder pattern can often be used to perform the characterization and/or identification. By selecting a collection of peaks that differentiate the crystalline solid form from other crystalline solid forms of the compound, one can rely on those peaks to both characterize the form and to identify the form in, for example, an unknown mixture. Additional data can be added, such as from another analytical technique or additional peaks from the powder pattern, to characterize and/or identify the form should, for instance, polymorphs be identified later.

Due to differences in instruments, samples, and sample preparation, peak values are reported with the modifier "about" in front of the peak values. This is common practice in the solid-state chemical arts because of the variation inherent in peak values. A typical precision of the 2θ x-axis value of a peak in a powder pattern is on the order of plus or minus 0.3° 2θ. Thus, a powder diffraction peak that appears at "about 19.0° 2θ" means that the peak could be between 18.7° 2θ and 19.3° 2θ when measured on most X-ray diffractometers under most conditions. Variability in peak intensity is a result of how individual crystals are oriented in the sample container with respect to the external X-ray source, the size of the crystallites, instrumental factors, and the temperature during the measurement.

X-Ray diffraction data presented herein was collected using a Bruker-AXS Model D8 Advance instrument. The powdered sample was prepared and mounted according to the manufacturer's recommendation. A Bruker-axs model D8 advance X-ray powder diffractometer was operated at 40 kV and 40.0 mA, and a VANTEC detector was used with a 1 mm antiscattering slit. The samples were scanned from a scattering angle of 3.7° 2θ to 30° 2θ, at a step size of 0.01° 2θ over a total scan time of 33 minutes.

FIG. 1 shows the X-ray powder diffraction patterns for three preparations of crystalline forms of (2S,4R)-1-(2-aminoacetyl)-4-benzamidopyrrolidine-2-carboxylic acid hydrochloride (traces 1-3), and one amorphous preparation of the compound (trace 4). The diffractogram of the amorphous material reveals no diffraction peaks, indicating that material is in fact amorphous and lacks crystallinity. Converting the amorphous material to a crystalline form yielded the material used to obtain the data shown in traces 1-3. The overlaid diffractograms reveal a consistent pattern of peaks and relative intensities for the crystalline hydrochloride monohydrate for a series of batches crystallized from acetone/water.

Figure 2:
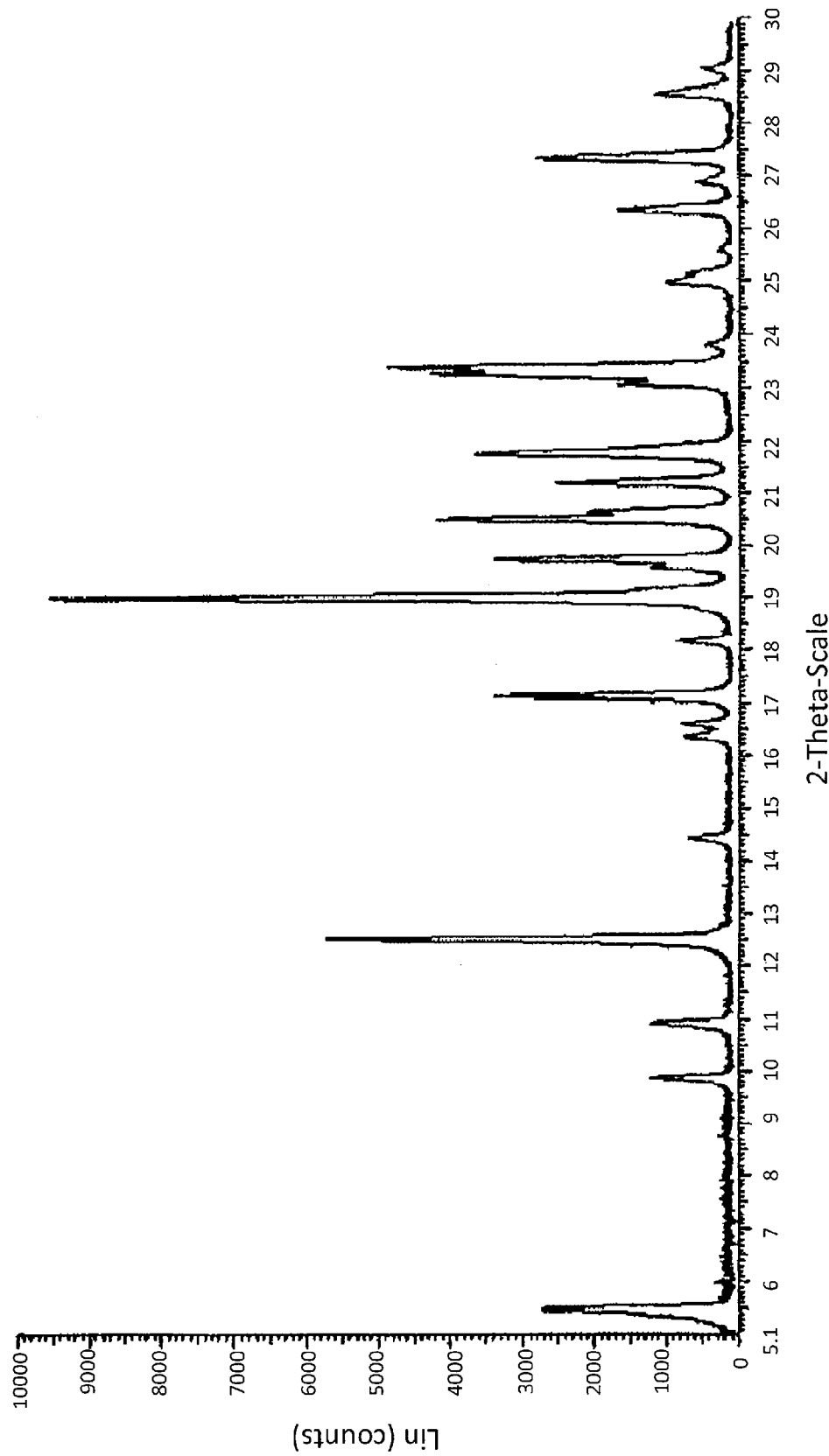
FIG. 2 is the X-ray powder diffraction pattern of (2S,4R)-1-(2-aminoacetyl)-4-benzamidopyrrolidine-2-carboxylic acid hydrochloride monohydrate.

FIG. 2 illustrates the diffractogram of the crystalline hydrochloride monohydrate from 5° 2θ to 30° 2θ. In some embodiments, the entire diffractogram and the peaks found therein is used to characterize the crystalline solid forms described herein. Thus, the crystalline solid forms are characterized by an X-ray powder diffraction pattern substantially as depicted in FIG. 2.

In some embodiments, a subset of the peaks in the pattern is used to characterize the crystalline form. Where another substance is suspected of being present, peaks common to the substances are ordinarily not useful to confirm the presence of either. In some embodiments, the subset of peaks having the greatest relative intensity are of interest. Any subset based on relative peak intensity may of course be modified to exclude certain peaks that overlap with those of other crystalline components suspected to be present.

The crystalline hydrochloride monohydrate compound is characterized by a pattern having peaks at about the scattering angles, and with about the relative intensities described in Table 1.

TABLE 1

| Scattering Angle (° 2θ) | Relative Intensity (%) |
|---|---|
| 5.4 | 28 |
| 9.8 | 12 |
| 10.9 | 12 |
| 12.5 | 60 |
| 14.4 | 6 |
| 16.3 | 8 |
| 16.6 | 8 |
| 17.1 | 36 |
| 18.2 | 9 |
| 19.0 | 100 |
| 19.2 | 14 |
| 19.6 | 12 |
| 19.7 | 35 |
| 20.5 | 44 |
| 20.7 | 22 |
| 21.2 | 26 |
| 21.8 | 37 |
| 23.1 | 17 |
| 23.3 | 44 |
| 23.4 | 51 |
| 23.8 | 5 |
| 25.0 | 10 |
| 25.1 | 7 |
| 25.6 | 3 |
| 26.4 | 17 |
| 26.9 | 6 |
| 27.4 | 29 |
| 28.6 | 12 |
| 29.1 | 5 |

The relative intensities of the peaks can vary depending on, for example, the sample preparation method, crystallite size, distribution of sizes, filters, instrument type, X-ray source, temperature, and the like. As mentioned above, these and other factors can also effect the scattering angle value. Furthermore, other peaks may be observed, or certain peaks listed in Table 1 may not be observed, depending on the instrumentation and the parameters used to record a diffractogram.

In some embodiments, the (2S,4R)-1-(2-aminoacetyl)-4-benzamidopyrrolidine-2-carboxylic acid hydrochloride monohydrate has X-ray powder diffraction peaks at about 12.5° 2θ and 19.0° 2θ. In some embodiments, the (2S,4R)-1-

(2-aminoacetyl)-4-benzamidopyrrolidine-2-carboxylic acid hydrochloride monohydrate has powder x-ray diffraction peaks at about 17.1° 2θ, 19.7° 2θ, 20.5° 2θ, 21.8° 2θ, 23.3° 2θ, and 23.4° 2θ. In some embodiments, the (2S,4R)-1-(2-aminoacetyl)-4-benzamidopyrrolidine-2-carboxylic acid hydrochloride monohydrate has powder x-ray diffraction peaks at about 5.4° 2θ, 20.7° 2θ, 21.2° 2θ, 23.1° 2θ, 26.4° 2θ, and 27.4° 2θ.

X-ray powder diffraction is just one of several analytical techniques available for characterizing and/or identifying crystalline solid forms. Spectroscopic techniques such as Raman (including microscopic Raman), infrared, and solid-state NMR spectroscopies may be used to characterize and/or identify crystalline solid forms. These techniques may also be used to quantify the amount of one or more crystalline solid forms in a mixture. Other methods for characterizing and/or identifying different crystalline solid forms of a compound include thermal techniques such as melting point or differential scanning calorimetry, thermal gravimetric analysis and dynamic vapor sorption.

Figure 3:
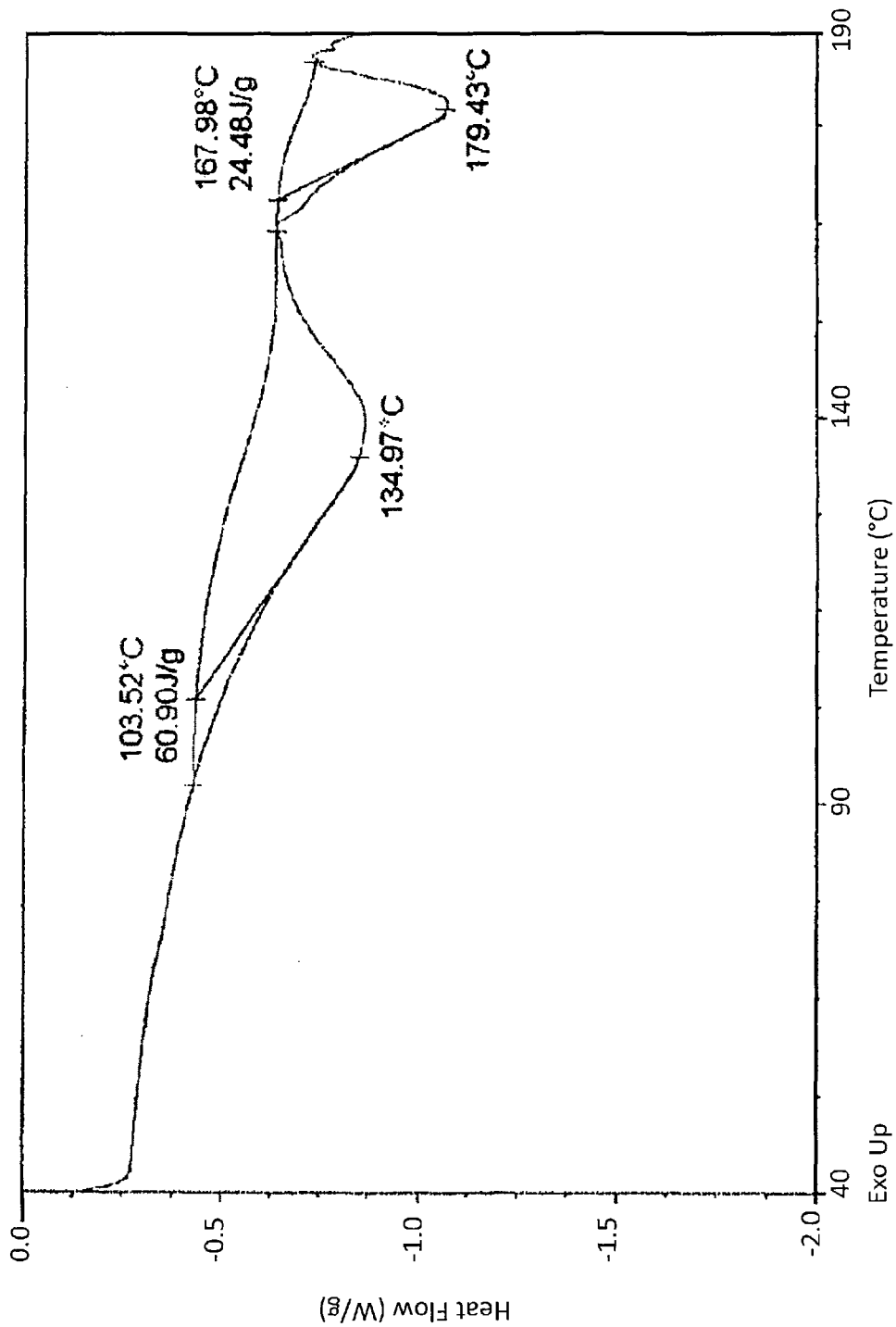
FIG. 3 is a differential scanning calorimetry ("DSC") analysis of (2S,4R)-1-(2-aminoacetyl)-4-benzamidopyrrolidine-2-carboxylic acid hydrochloride monohydrate.

In some embodiments, the (2S,4R)-1-(2-aminoacetyl)-4-benzamidopyrrolidine-2-carboxylic acid hydrochloride monohydrate is characterized by differential scanning calorimetry ("DSC"). A DSC trace is shown in FIG. 3. DSC data were collected using a model Q1000 DSC from TA Instruments. Samples were analyzed by scanning the temperature from 40° to 200° C. at a scan rate of 10° C./min while under a dinitrogen gas purge of 50 mL/min. The calorimetric events observed in the DSC trace may vary in temperature or magnitude depending on, for example, the sample preparation method, crystallite size, impurities, type of instrument, calibration, heating rate, and the like, with variations in the temperature of about 5° C. possible.

As shown in FIG. 3, the DSC thermogram of the (2S,4R)-1-(2-aminoacetyl)-4-benzamidopyrrolidine-2-carboxylic acid hydrochloride monohydrate is characterized by two peaks. The first peak is observed at about 135° C., with an onset temperature of about 104° C., and is believed to correspond to loss of the water of hydration. The second peak is observed at about 180° C., with an onset temperature of about 168° C., and is believed to represent a melting event. Accordingly, in some embodiments, the (2S,4R)-1-(2-aminoacetyl)-4-benzamidopyrrolidine-2-carboxylic acid hydrochloride monohydrate is characterized by a DSC trace substantially as depicted in FIG. 3. In some embodiments, the (2S,4R)-1-(2-aminoacetyl)-4-benzamidopyrrolidine-2-carboxylic acid hydrochloride monohydrate is characterized by having two endothermic transitions with onset temperatures of about 104° C. and about 168° C.

Figure 4:
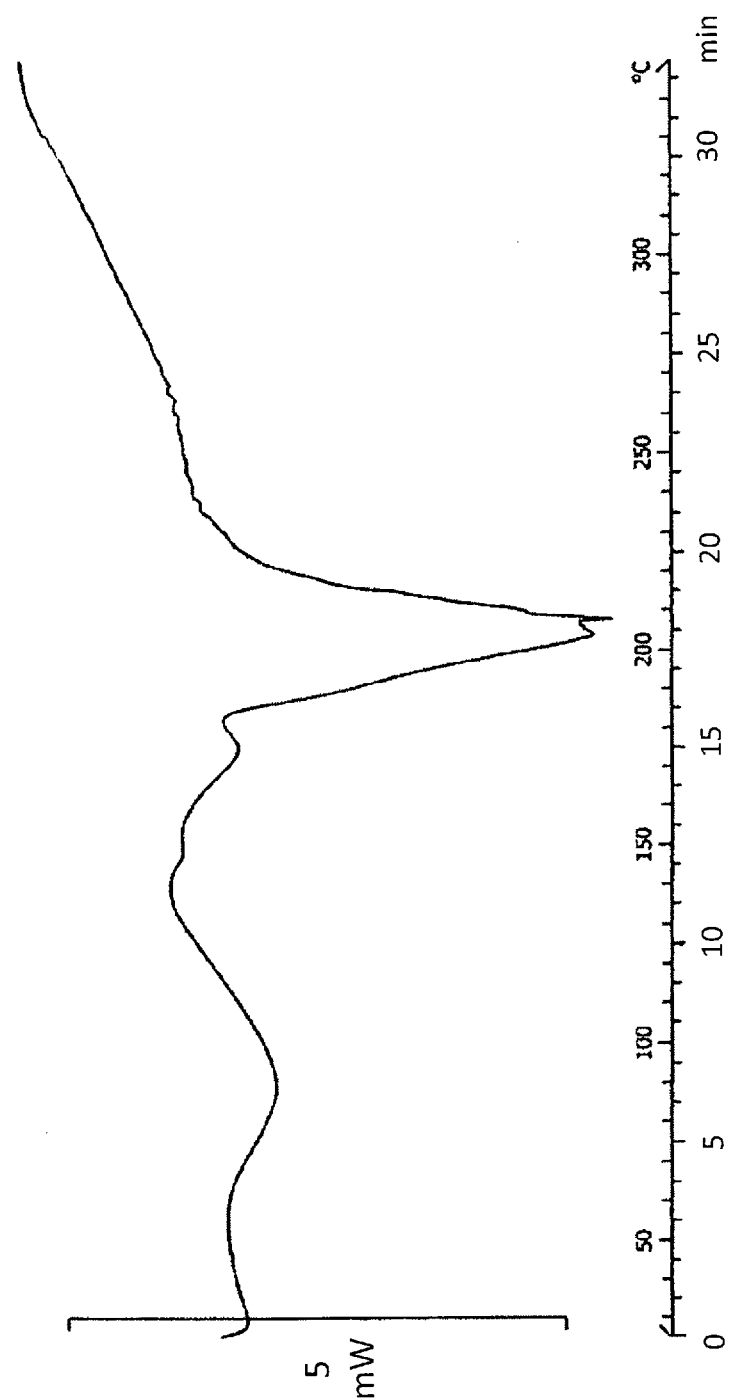
FIG. 4 is a DSC analysis of amorphous (2S,4R)-1-(2-aminoacetyl)-4-benzamidopyrrolidine-2-carboxylic acid hydrochloride.

As shown in FIG. 4, the DSC thermogram of amorphous (2S,4R)-1-(2-aminoacetyl)-4-benzamidopyrrolidine-2-carboxylic acid hydrochloride is characterized by a broad endothermic transition between about 185° C. and 230° C. The response of the material to DSC analysis is representative of the behavior typically observed for amorphous materials.

In some embodiments, the (2S,4R)-1-(2-aminoacetyl)-4-benzamidopyrrolidine-2-carboxylic acid hydrochloride monohydrate is characterized by thermal gravimetric analysis ("TGA"). A TGA trace is shown in FIG. 4. TGA data were collected using a model TGA/SDTA 851e from Mettler Toledo. Samples were analyzed by scanning the temperature from 30° to 250° C. at a scan rate of 10° C./min while under a dinitrogen gas purge of 40 mL/min. The thermogravimetric events observed in the TGA trace may vary in temperature or magnitude depending on, for example, the sample preparation method, crystallite size, impurities, type of instrument, calibration, heating rate, and the like, with variations in the temperature of about 5° C., or in the magnitude of a few percent possible.

Figure 5:
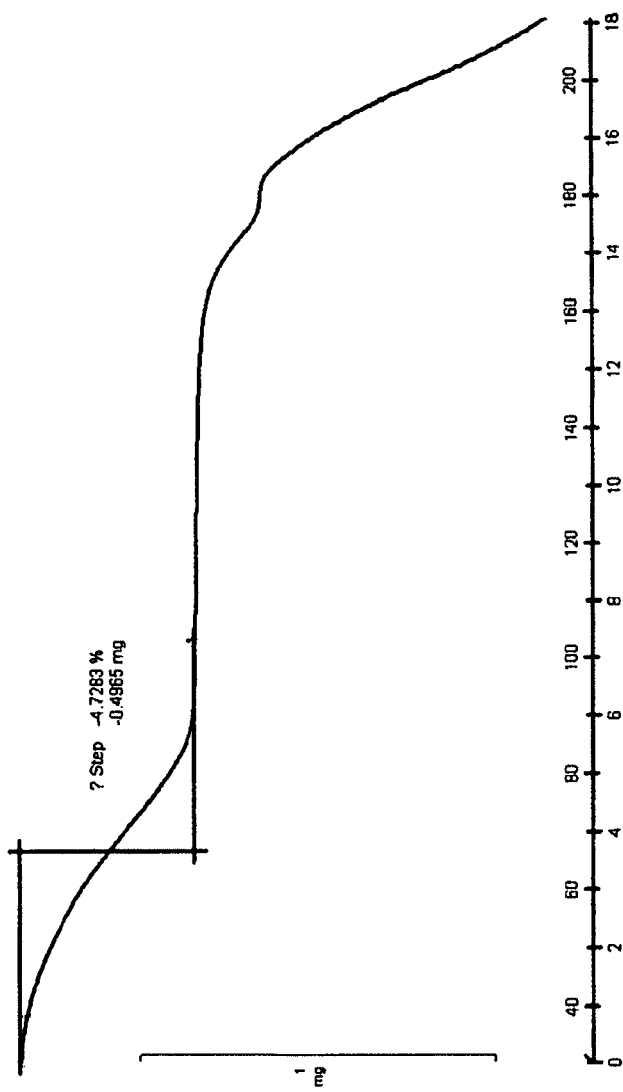
FIG. 5 is a thermal gravimetric analysis ("TGA") of (2S,4R)-1-(2-aminoacetyl)-4-benzamidopyrrolidine-2-carboxylic acid hydrochloride monohydrate.

As shown in FIG. 5, the TGA thermogram of the (2S,4R)-1-(2-aminoacetyl)-4-benzamidopyrrolidine-2-carboxylic acid hydrochloride monohydrate is characterized primarily by a weight loss of about 4.7% in one step. The step is roughly complete when the temperature ramp reaches about 90° C. The weight loss is believed to correspond to a loss of the water of the monohydrate crystal form. The theoretical water content of a monohydrate form is 5.2%. It is recognized by those of skill in the art that the amount of water in a hydrate can vary depending on the methods and conditions of crystallization, and the handling of the crystals thereafter. Thus, in some embodiments, the molar ratio of the hydrate present in the crystalline form is about 0.5 to about 1.2, from about 0.7 to about 1.0, or about 1.0. Accordingly, in some embodiments, the (2S,4R)-1-(2-aminoacetyl)-4-benzamidopyrrolidine-2-carboxylic acid hydrochloride monohydrate is characterized by a TGA trace substantially as depicted in FIG. 5. In some embodiments, the (2S,4R)-1-(2-aminoacetyl)-4-benzamidopyrrolidine-2-carboxylic acid hydrochloride monohydrate is characterized by having a weight loss of about 5.0% upon an increase in temperature to about 100° C. In some embodiments, the (2S,4R)-1-(2-aminoacetyl)-4-benzamidopyrrolidine-2-carboxylic acid hydrochloride monohydrate is characterized by having a weight loss of about 4.7% upon an increase in temperature to about 90° C.

In some embodiments, the (2S,4R)-1-(2-aminoacetyl)-4-benzamidopyrrolidine-2-carboxylic acid hydrochloride monohydrate is characterized by dynamic vapor sorption ("DVS"). A DVS trace in shown in FIG. 6. DVS data were collected using Dynamix Vapor Sorption Apparatus (DVS-1) made by Surface Measurement System Ltd. Samples were analyzed by subjecting them to a series of relative humidity (RH) conditions at 25° C. The relative humidity was scanned from about 0% to about 90%.

Figure 6:
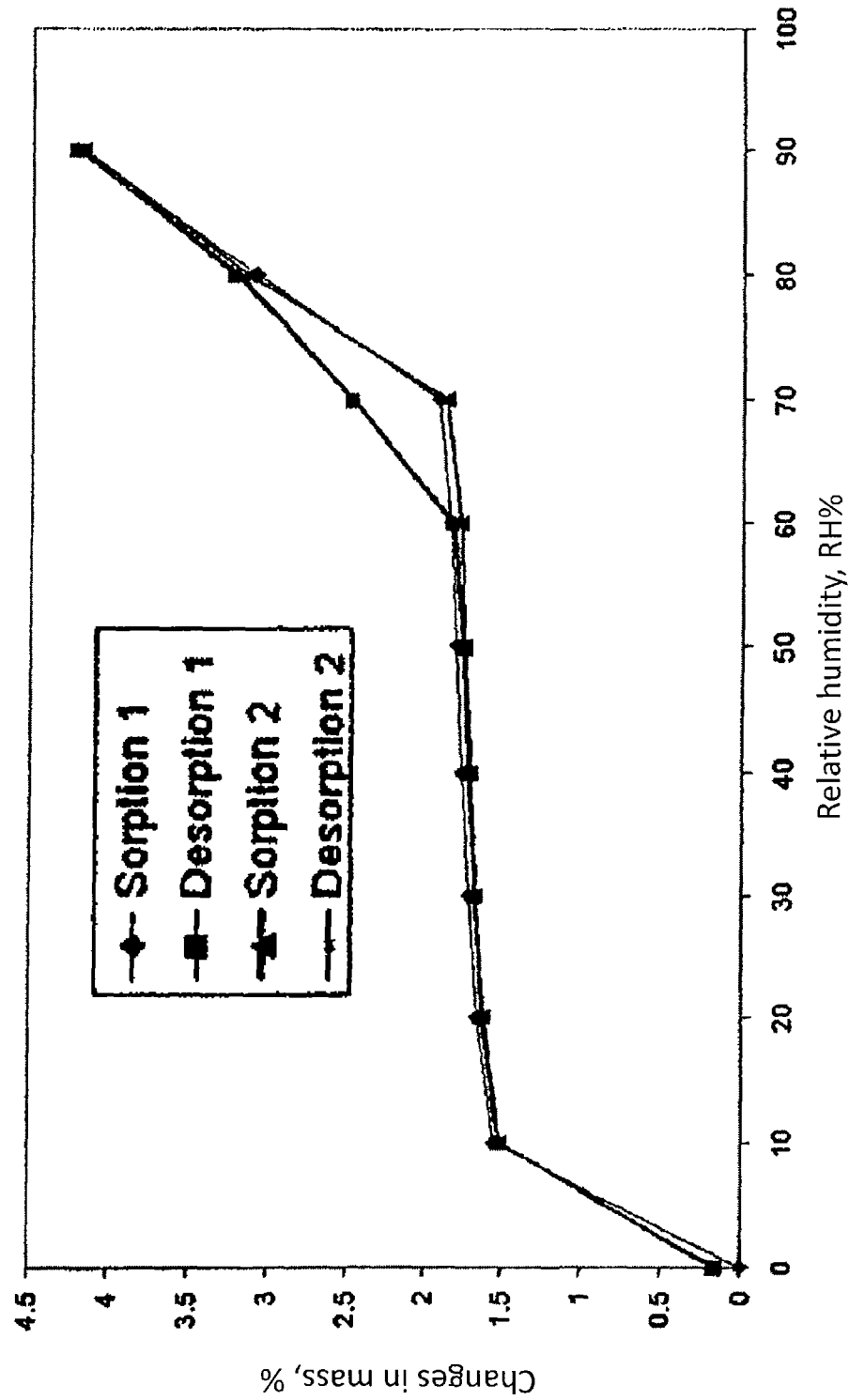
FIG. 6 is a dynamic vapor sorption analysis of (2S,4R)-1-(2-aminoacetyl)-4-benzamidopyrrolidine-2-carboxylic acid hydrochloride monohydrate.

As shown in FIG. 6, the DVS trace of the (2S,4R)-1-(2-aminoacetyl)-4-benzamidopyrrolidine-2-carboxylic acid hydrochloride monohydrate is characterized by reversible change of mass of about 1.5% between 0% RH and 10% RH, followed by a relatively stable mass between 10% RH and about 70% RH, followed by about a 2.5% reversible mass change between about 70% RH and 90% RH. The DVS trace indicates that although the crystalline forms described herein may be prone to gain water at high humidity, the sorbed water is reversibly lost and does not appear to adversely affect the integrity of the crystalline form.

Figure 7:
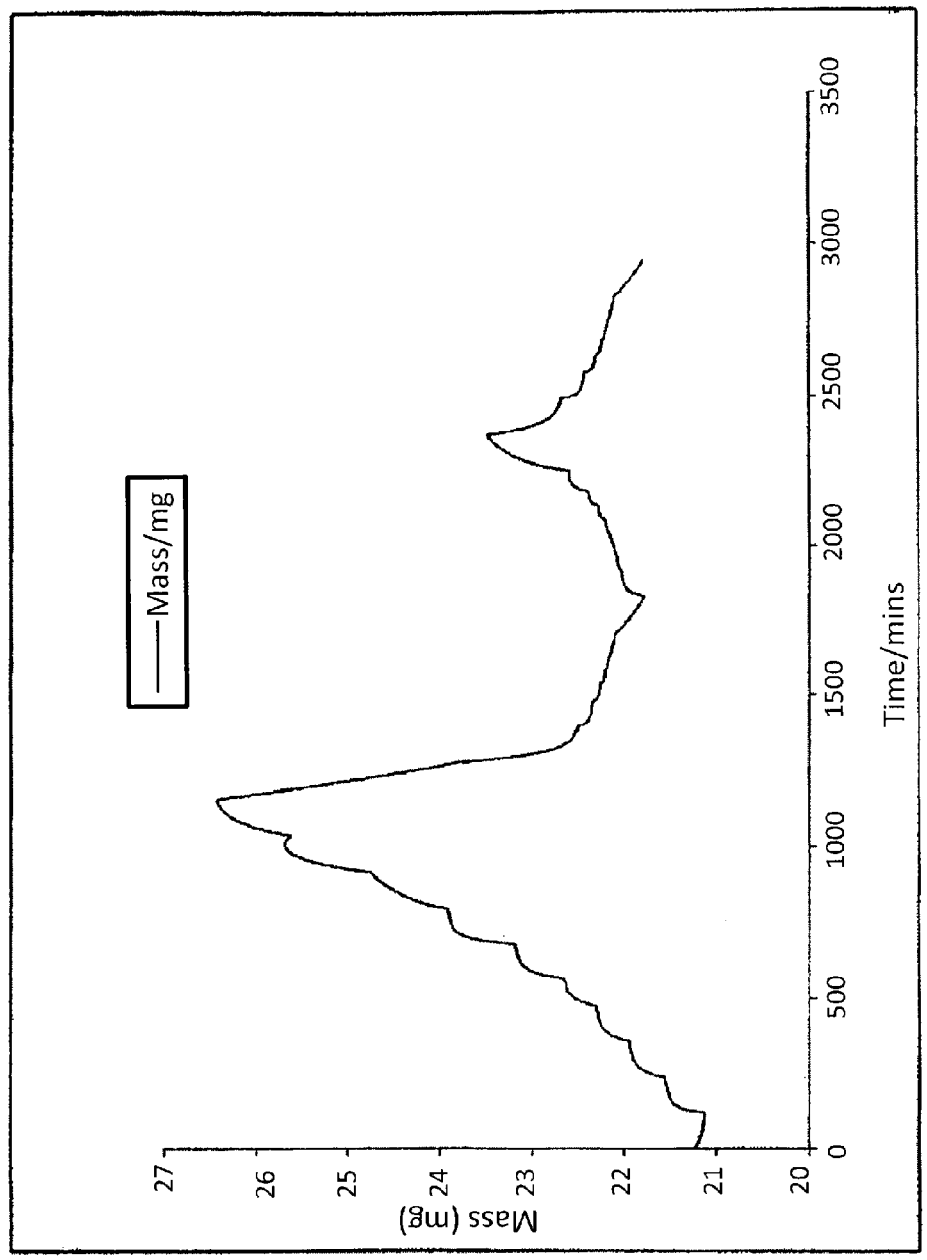
FIG. 7 is dynamic vapor sorption analysis of amorphous (2S,4R)-1-(2-aminoacetyl)-4-benzamidopyrrolidine-2-carboxylic acid hydrochloride.

As shown in FIG. 7, the DVS trace of the amorphous form of (2S,4R)-1-(2-aminoacetyl)-4-benzamidopyrrolidine-2-carboxylic acid hydrochloride is characterized by a large increase in weight when first exposed to high humidity and that these changes are not reversible upon cycling of the relative humidity. The amorphous form increased in mass by 21.7% when the relative humidity increased from 0% RH to 90% RH in the first cycle, from 0 to about 1200 min. On return to 0% RH, from about 1200 min to about 1800 min, the sample did not return to its original mass, and on repeating the increase to 90% RH, from about 1800 min to about 2400 min, the gain in mass was not nearly as large as in the first cycle. Inspection of the sample following the experiment revealed that the original free-flowing powder was transformed into a solid mass by the change in humidity. These results indicate that the amorphous form is not stable to environmental changes in humidity.

The compounds described herein can serve as medicaments in their pure form or as pharmaceutical formulations, which can be administered via any acceptable method known in the art, either singly or in combination. Pharmaceutical formulations generally comprise a compound described herein in admixture with one or more pharmaceutically acceptable carriers. Such compositions can be formulated to oral administration (including buccal cavity or sublingually) or by parenteral administration (including intravenous (i.v.), subcutaneous (s.c.), intramuscular (i.m.), intraperitoneal (i.p.)) administration. Other administration routes include epidural, rectal, intranasal or dermal administration or by pulmonary inhalation. In some embodiments, sustained release of the compounds described herein are used. In some embodiments, the compositions are in the form of solid or liquid formulations and methods for their preparation are generally described in "Remington's Pharmaceutical Sciences", 17th Ed., Alfonso R. Gennaro (Ed.), Mark Publishing Company, Easton, Pa., U.S.A., 1985.

In some embodiments, the carrier is in the form of one or more substances chosen from vehicles, diluents, buffering agents, tonicity adjusting agents, preservatives and stabilizers. The excipients constituting the carrier should be compatible with the active pharmaceutical ingredient(s) and are capable of stabilizing the compounds without being deleterious to the subject being treated.

A form of repository or sustained-release formulation can be used so that therapeutically effective amounts of the preparation are delivered into the bloodstream over many hours or days following administration of the compound or composition, e.g., by transdermal injection or deposition. Formulations suitable for sustained release include biodegradable polymers, such as L-lactic acid, D-lactic acid, DL-lactic acid, glycolide, glycolic acid, and isomers thereof. Similarly, the carrier can include any sustained release material known in the art, such as glyceryl monostearate or glyceryl distearate, alone or mixed with a wax.

Other sustained release formulations can include, but are not limited to, formulations that include at least one of the compounds disclosed herein combined with liposomes, microspheres, emulsions or micelles and liquid stabilizers.

The doses of the compounds and compositions described herein required for the desired therapeutic effects will depend upon on the potency of the compound, the particular composition used and the route of administration selected. "A therapeutically effective amount" refers to an amount that reduces symptoms of a given condition or pathology, and in some embodiments, which normalizes physiological responses in a subject with the condition or pathology. Reduction of symptoms or normalization of physiological responses can be determined using methods routine in the art and can vary with a given condition or pathology.

In some embodiments, a therapeutically effective amount of one or more compounds or pharmaceutical formulations is an amount which restores a measurable physiological parameter to substantially the same value (preferably to within ±30%, more preferably to within ±20%, and still more preferably, to within ±10% of the value) of the parameter in a subject without the condition or pathology.

The therapeutically effective amount will be determined by the skilled person taking into account such factors as potency of the drug, age and constitution of the patient, body weight, pharmacokinetic profile of the drug, and in general the drug will be prescribed for each patient or group of patients. However, in some embodiments, the therapeutically effective amount of the compound is at least about 10 µg/kg body weight/day, such as at least about 100 µg/kg body weight/day, at least about 300 µg/kg body weight/day, and at least about 1000 µg/kg body weight/day. In some embodiments, the therapeutically effective amount of the compound is at most about 100 mg/kg body weight/day, such as at most about 50 mg/kg body weight/day and at most about 10 mg/kg body weight/day. In some embodiments the therapeutically effective amount of the compound will be about 100 µg/kg body weight/day, about 300 µg/kg body weight/day or about 1000 µg/kg body weight. In some embodiments, the compounds are administrated in the range of about 0.001 g to 10 g per patient per day. For example, in some embodiments, the compounds are administered in the range from about 1 mg to about 1000 mg per patient per day, from about 10 mg to about 100 mg per patient per day, or about 50 mg per patient per day.

The most suitable dosing regimen can best be determined by a medical practitioner for each patient individually. The optimal dosing regimen with the compounds and pharmaceutical formulations described herein depends on factors such as the particular disease or disorder being treated, the desired effect, and the age, weight or body mass index, and general physical conditions of the patient. The administration can be conducted in a single unit dosage form to alleviate acute symptoms or as a continuous therapy in the form of multiple doses over time. Alternatively, continuous infusion systems or slow release depot formulations can be employed. Two or more compounds or pharmaceutical formulations described herein can be co-administered simultaneously or sequentially in any order. In addition, the compounds and compositions can be administered in a similar manner for prophylactic purposes. Ultimately, the best dosing regimen will be decided by the attending physician for each patient individually.

Also provided are methods of preventing or treating a condition comprising administering to a subject in need thereof (e.g., a human being) a therapeutically effective amount of a compound or pharmaceutical formulation as described herein. Examples of conditions that can be treated or prevented using the compounds or pharmaceutical formulations described herein include, but are not limited to, cardiovascular disease (e.g., atrial fibrillation, atrial flutter, ventricular tachycardia or ventricular fibrillation); osteoporosis; inflammation of airway epithelium; disorders of alveolar tissue; bladder incontinence; impaired hearing, such as due to diseases of the cochlea; endothelial lesions; diabetes including diabetic retinopathy and diabetic neuropathy; CNS related conditions; ischemia (e.g. ischemia of the central nervous system, spinal cord, brain or brain stem); dental tissue disorders including periodontal disease; kidney diseases; haematologic manifestations (e.g., anaemia, leukopenia, thrombocytopenia, and pancytopenia) especially following treatment with cytostatic compounds or irradiation therapy; wounds such as superficial wounds and deep wounds resulting from trauma; erectile dysfunction; urinary bladder incontinence; neuropathic pain; subchronic and chronic inflammation; cancer; failure of bone marrow and stem cell transplantation; conditions which arise during transplantation of cells and tissues or during medical procedures such as surgery; conditions caused by an excess of reactive oxygen species, free radicals or nitric oxide; diseases or disorders of pregnancy (e.g., preeclampsia and preterm labor); and stroke.

The compounds or pharmaceutical formulations described herein can be used to maintain normal sinus rhythm (NSR) following cardioversion of atrial fibrillation (AF), to prevent post-operative AF following cardiac surgery, and to pharmacologically cause cardioversion of AF.

The compounds and pharmaceutical formulations described herein can facilitate and/or maintain the intercellular communication mediated by gap junctions. In one aspect, the compounds and pharmaceutical formulations described herein target the same cells targeted by AAP, AAP10, HP5, and/or functional analogues thereof, i.e. the compounds are able to modulate the function of these cells by agonizing or antagonizing the function of AAP, AAP10, HP5, and/or functional analogues thereof. The embodiments are, however, not limited to compounds having specific AAP agonistic or antagonistic properties. Some embodiments also relate to the preparation and use of pharmaceutical formulations for the treatment of pathologies which can be associated with impaired intercellular gap junction communication and methods for using these compositions, e.g., as disclosed in WO 02/077017 "New Medical Uses of Intercellular Communication Facilitating Compounds."

Some embodiments also provide methods of treating a subject having, or preventing a subject at risk from developing, a condition associated with impaired GJIC (e.g., cardiac arrhythmia or osteoporosis) comprising administering a therapeutically effective amount of any of the compounds or pharmaceutical formulations described herein. Individuals who can be treated using compounds described herein include, but are not limited to, animals, preferably mammals, e.g., rodents (including mice, rats, hamsters, and lagomorphs, such as rabbits), dogs, pigs, goats (generally any domestic animal), and primates. In some embodiments, the subject is a human being.

Examples of conditions which can be treated or prevented using compounds and pharmaceutical formulations described herein include, but are not limited to, cardiovascular disease; osteoporosis; inflammation of airway epithelium; disorders of alveolar tissue; bladder incontinence; impaired hearing (e.g. due to diseases of the cochlea); endothelial lesions; diabetes (Type I or Type II) and diabetic complications (including diabetic retinopathy and diabetic neuropathy); atherosclerosis; CNS related conditions; seizures; ischemia (e.g. ischemia of the central nervous system, spinal cord, brain or brain stem); dental tissue disorders (including periodontal disease); kidney diseases; haematologic manifestations (e.g., anaemia, leukopenia, thrombocytopenia, and pancytopenia, especially following treatment with cytostatic compounds or irradiation therapy); wounds (e.g., superficial wounds and deep wounds resulting trauma); bone fracture; erectile dysfunction; urinary bladder incontinence; neuropathic pain; subchronic and chronic inflammation; cancer; failure of bone marrow and stem cell transplantation; conditions which arise during transplantation of cells and tissues or during medical procedures such as surgery; conditions caused by an excess of reactive oxygen species and/or free radicals and/or nitric oxide; diseases or disorders of pregnancy (e.g., preeclampsia and preterm labor); female infertility; and stroke. Compounds and pharmaceutical formulations described herein can also be used to induce labor (e.g., by facilitating the effect of oxytocin on uterus contraction).

Some embodiments provide a pharmacologically active antiarrhythmic compound for treatment or prevention of arrhythmias and thrombotic complications arising during cardiovascular disorders, such as acute ischemic heart disease (e.g., stable angina pectoris, unstable angina pectoris, acute myocardial infarction), congestive heart failure (e.g., systolic, diastolic, high-output, low-output, right or left sided heart failure), congenital heart diseases, cor pulmonale, cardiomyopathies, myocarditis, hypertensive heart disease, during coronary revascularization, and the like. In some embodiments, compounds described herein can be used to treat and/or prevent bradyarrhythmias (e.g., due to disease in sinus node, AV node, bundle of His, right or left bundle branch), and tachyarrhythmias associated with reentry (e.g., atrial premature complexes, AV junctional complexes, ventricular premature complexes, atrial fibrillation, atrial flutter, paroxysmal supraventricular tachycardia, sinus node reentrant tachycardia, AV nodal reentrant tachycardia, and non-sustained ventricular tachycardia). Furthermore, compounds and pharmaceutical formulations described herein can be useful for alleviating conditions wherein slowing of conduction velocity is an important factor, e.g. ventricular tachycardia, ventricular fibrillation, and atrial fibrillation. Compounds and pharmaceutical formulations described herein can be administered either alone or in combination with other antiarrhythmic compounds, such as class I agents (e.g., lidocaine), class II agents (e.g., metoprolol or propranolol), class III agents (e.g., amiodarone or sotalol) or class IV agents (e.g., verapamil).

Compounds and pharmaceutical formulations described herein can also be used to treat or prevent one or more of reentry arrhythmia, ventricular reentry (e.g., arising during acute myocardial infarction, chronic myocardial infarction, stable angina pectoris and unstable angina pectoris), infectious or autonomic cardiomyopathy, atrial fibrillation, repolarization alternans, monomorphic ventricular tachycardia, T-wave alternans, bradyarrhythmias, reduced contractility of cardiac tissue, thrombosis, and the like.

Additional functions in which endothelial gap-junction intercellular communication has been implicated are the migratory behavior of endothelial cells after injury, angiogenesis, endothelial growth and senescence and the coordination of vasomotor responses (Christ et al. Braz. J Med. Biol. Res., 33, 423-429 (2000)). Therefore, compounds and pharmaceutical formulations described herein can be used to enhance conducted vascular responses and to improve blood supply during conditions with increased metabolic demand (e.g., physical exercise, tachycardia), and during ischemia.

Compounds and pharmaceutical formulations described herein can be used to cytoprotect a tissue or organ of a mammal in need of such treatment. Cytoprotecting refers to reducing, preventing or alleviating symptoms associated with unwanted cell swelling. Particular tissues and organs that will benefit from the method include those confined or otherwise impacted by a fiborous capsule such as heart or kidney. Also included are tissues associated with bone such as brain, spinal cord and bone marrow.

Compounds and pharmaceutical formulations described herein can be used to prevent or treat ischemic injury in the organs of a mammal in need of such treatment, including, for example, the heart, central nervous system, kidney, gastrointestinal tract, liver, lungs, and limbs.

Some embodiments provide the use of the compounds and pharmaceutical formulations described herein to treat or prevent haematologic manifestations following treatment with cytostatic compounds or irradiation therapy. Impaired haematopoiesis recovery is observed in patients after 5-fluorouracil (5-FU) cytostatic treatment. This includes absence of recovery of peripheral blood counts, including severe neutropenia, severe anemia with reticulocytopenia and presence of abnormal peripheral erythrocytes and severe thrombocytopenia. In addition, 5-8-fold decreases of bone marrow cellularity and hematopoietic progenitor content (granulomacrophagic colony-forming-units (CFU-GM), erythroid burst forming units (BFU-E), mixed colony forming units (CFU-mix), and overall colony forming units (CFU-C) in bone marrow are observed. Also provided are the treatment or prevention of general clinical situations commonly associated with iatrogenic pancytopenia.

Compounds and pharmaceutical formulations described herein can be use to treat or prevent osteoporosis. It is known that that GJIC is important in bone formation. The efficacy of the compounds can be assessed, for example, by an increase in osteoblast activity in a standard osteoblast activity assay which measures either calcium wave formation and/or alkaline phosphatase activity of osteoblast cells in the presence of the compounds. Alkaline phosphatase activity also can be used to provide a measure of osteoblast activity using standard calorimetric assays.

The present disclosure will be further developed in the following examples. It should be understood that these examples are for illustrative purposes only, and are not to be construed as limiting the present disclosure in any manner.

EXAMPLES

Representative, but non-limiting syntheses of representative compounds are shown in Examples 1 through 5.

Example 1

Synthesis of (2S,4R)-1-(2-Aminoacetyl)-4-benzamidopyrrolidine-2-carboxylic acid hydrochloride

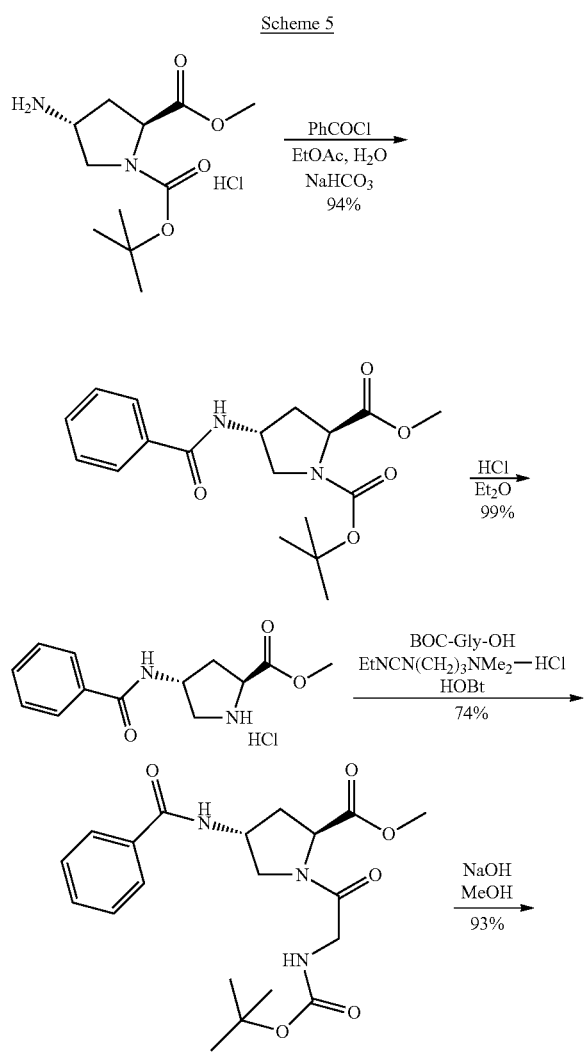

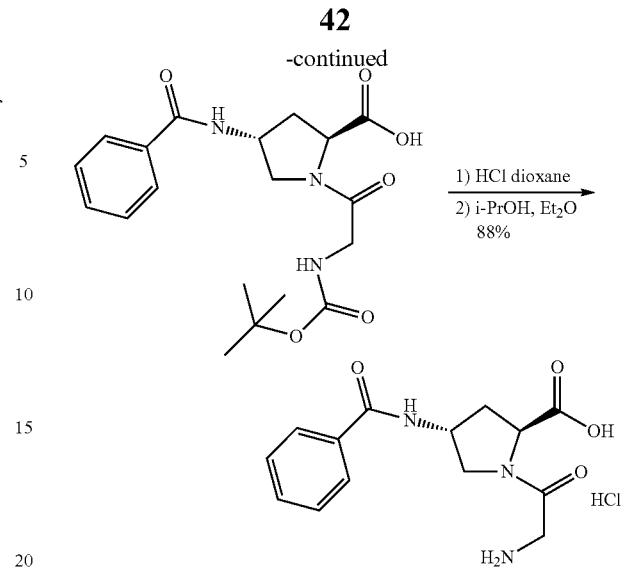

Step 1: Synthesis of (2S,4R)-1-tert-Butyl-2-methyl-4-benzamidopyrrolidine-1,2-dicarboxylate To a solution of NaHCO$_3$ (58.64 g, 0.698 mol) in water (625 mL) N-Boc-trans-4-amino-L-proline methyl ester hydrochloride (50 g, 0.1745 mol, CNH Technologies, 98%) was added in portions, followed by EtOAc (500 mL). The mixture was cooled to 0° C. A solution of benzoyl chloride (20.26 mL, 0.1745 mol) in EtOAc (100 mL) was added over 25 min at 0° C. The reaction mixture was stirred at 0° C. for 1 h. Phases were separated. Aqueous phase was extracted 2×200 mL of EtOAc. Combined organic fraction was washed with 200 mL of 1N HCl, 100 mL of saturated NaHCO$_3$ solution, 100 mL of brine, dried over MgSO$_4$, and concentrated to afford 60.67 g of the title product as heavy oil (99.8% yield; 94% yield adjusted to residual EtOAc). $^1$H NMR (CDCl$_3$, δ, ppm; for two conformers): 7.78-7.7 (m, 2H), 7.56-7.4 (m, 3H), 6.25-6.1 (m, 1H), 4.8-4.67 (m, 1H), 4.51-4.41 (m, 0.4H), 4.34 (dd, J=7, 7 Hz, 0.6H), 3.97-3.84 (m, 1H), 3.76 (s, 3H), 3.52 (dd, J=11, 4 Hz, 0.6H), 3.39 (dd, J=11, 4 Hz, 0.4H), 2.47-2.21 (m 2H), 1.46 (s, 3.6H), 1.43 (s, 5.4H). MS (m/z, positive ESI, for M+Na): 371.

Step 2: Synthesis of (2S,4R)-Methyl 4-benzamidopyrrolidine-2-carboxylate hydrochloride (2S,4R)-1-tert-Butyl-2-methyl-4-benzamidopyrrolidine-1,2-dicarboxylate (60.19 g, contains 5.6% EtOAc; 0.1631 mol) was dissolved in Et$_2$O (100 mL), and the solvent was evaporated in vacuum to remove residual EtOAc. The residual oil was dissolved in Et$_2$O (100 mL). 2N HCl solution in Et$_2$O (700 mL) was added (mild exotherm; precipitation commenced after ca. 5 min). The mixture was stirred at ambient temperature for 21 h. At that point, 200 mL of 2N HCl solution in Et$_2$O were added, and the mixture was stirred for additional 24 h. The precipitate was filtered, washed with 500 mL of diethyl ether, and dried in vacuum at ambient temperature for 24 h to afford 46.03 g of the title product (99% yield). $^1$H NMR (CD$_3$OD, δ, ppm): 7.91-7.84 (m, 2H), 7.6-7.44 (m, 3H), 4.78 (t, J=8.5 Hz, 1H), 4.69-4.59 (m, 1H), 3.77 (dd, J=12, 6.6 Hz, 1H), 3.52 (dd, J=12, 5 Hz, 1H), 2.67-2.5 (m, 2H). MS (m/z, positive ESI, for M+H): 249.

Step 3: Synthesis of (2S,4R)-Methyl 4-benzamido-1-(2-(tert-butoxycarbonylamino)acetyl)pyrrolidine-2-carboxylate To a solution of Boc-Gly-OH (28.13 g, 0.1606 mol) and 1-hydroxybenzotriazole (0.1686 mol, 25.64 g; contains 11.12 wt % H₂O) in THF (1.3 L) was added N-(3-dimethylaminopropyl)-N'-ethylcarbodiimide hydrochloride (0.1686 mol, 32.328 g) (Flask A). The mixture was stirred at ambient temperature for 4 h, then the stirring was stopped, and oily residue was allowed to settle.

In a separate flask (Flask B), NaOH (0.1606 mol; 32 mL of 5N solution) was added to a suspension of (2S,4R)-methyl 4-benzamidopyrrolidine-2-carboxylate hydrochloride (0.1606 mol, 45.73 g) in THF (0.52 L) over 15 min. The mixture was stirred at ambient temperature for 10 min (the solids mostly dissolved). The solution of HOBt ester prepared above (Flask A) was added to the reaction mixture (Flask B) at ambient temperature over 15 min, leaving the oily residue behind. The residue in Flask A was washed with 250 mL of THF. The THF solution was demayted from the heavy oil, and added to the mixture in Flask B. The reaction mixture was stirred at ambient temperature for 40 min. Water (500 mL) was added, and the mixture was concentrated in vacuum to remove THF (~550 mL residual volume). EtOAc (500 mL) was added, followed by brine (300 mL). Phases were separated. Aqueous phase was extracted with 2×300 mL of EtOAc. Combined organic fraction was washed 2×250 mL of 1N HCl, 2×250 mL of sat. NaHCO₃ solution, 150 mL of brine, dried over MgSO₄, and concentrated to afford 48.31 g of the title product as a foamy solid (74% yield). $^1$H NMR (CDCl₃, δ, ppm; for two conformers): 7.81-7.72 (m, 2H), 7.57-7.39 (m, 3H), 6.41 (d, J=6 Hz, 0.8H), 6.25 (d, J=6 Hz, 0.2H), 5.32 (br. s, 1H), 4.88-4.74 (m, 1H), 4.65 (t, J=7 Hz, 1H), 4.11-3.86 (m, 2H), 3.83-3.78 (m, 1H), 3.76 (s, 3H), 3.69-3.56 (M, 1H), 2.65-2.3 (m, 2 H), 1.43 (s, 9H). MS (m/z, positive ESI, for M+Na): 428.

Step 4: Synthesis of (2S,4R)-4-Benzamido-1-(2-(tert-butoxycarbonylamino)acetyl)pyrrolidine-2-carboxylic acid To a solution of (2S,4R)-methyl 4-benzamido-1-(2-(tert-butoxycarbonyl-amino)acetyl)pyrrolidine-2-carboxylate (23.33 g, 0.0575 mol) in methanol (450 mL) NaOH (0.2875 mol, 144 mL of 2N aqueous solution) was added at −1 to 1° C. over 15 min. The mixture was stirred at −5 to 1° C. for 2.5 h. HCl (0.2875 mol, 144 mL of 2N aqueous solution) was added at −3 to 1° C. over 25 min. MeOH was distilled off in vacuum. 500 mL of EtOAc were added. Aqueous phase was saturated with NaCl. Phases were separated. Aqueous phase was extracted with 2×250 mL of EtOAc. Combined EtOAc solution was dried over MgSO₄, and concentrated to afford 22.54 g of the title product as a white foamy solid (contains 6.6 wt % EtOAc; 94% yield adjusted to residual EtOAc). $^1$H NMR (CD₃OD, δ, ppm): 7.87-7.79 (m, 2H), 7.58-7.42 (m, 3H), 4.81-4.7 (m 1H), 4.69-4.56 (m, 1H), 4.05-3.72 (m, 3H), 3.67-3.49 (m, 1H), 2.64-2.28 (m, 2H), 1.43 (s, 9H). MS (m/z, positive ESI) for M+H: 392; for M+Na: 414.

Step 5: Synthesis of (2S,4R)-1-(2-Aminoacetyl)-4-benzamidopyrrolidine-2-carboxylic acid hydrochloride (2S,4R)-4-Benzamido-1-(2-(tert-butoxycarbonylamino)acetyl)pyrrolidine-2-carboxylic acid (21.97 g; contains 6.6 wt EtOAc; 0.0524 mol, adjusted to residual EtOAc) was dissolved in dioxane (100 mL). The solvent was evaporated in vacuum to remove residual EtOAc. The residue was dissolved in anhydrous dioxane (200 mL). HCl (100 mL of freshly prepared ~3.6 N solution in dioxane) was added at 10-12° C. The solution was allowed to warm up to ambient temperature (precipitation commenced after about 2 min). The reaction mixture was stirred at ambient temperature for 21 h, at which time 30 mL of ~3.6N HCl solution were added, and the mixture was stirred for additional 5.5 h. Precipitated solids were filtered using N₂ pressure, washed with 4×25 mL of dioxane, and dried in vacuum at room temperature for 24 h to afford 18.7 g of crude product as white solid.

The product was dissolved in i-PrOH (104 mL). 210 mL of diethyl ether were added over 1 h (precipitate formed immediately upon ether addition). The mixture was stirred for 1 h, filtered using N₂ pressure, washed with 2×50 mL of 3:1 Et₂O: i-PrOH solution, and dried in vacuum at room temperature for 24 h and at 40° C. for 48 h to afford 15.7 g of the title compound.

The product was combined with 12.77 g of the product from a previous batch, dissolved in 2 L of water, and the solution was lyophilized to obtain 26.85 g of the title compound. $^1$H NMR (DMSO-d₆, δ, ppm, for two conformers): 8.77 (d, J=7 Hz, 0.8H), 8.71 (d, J=7 Hz, 0.2H), 8.68-7.95 (br, 2H), 7.92-7.83 (m, 2H), 7.59-7.43 (m, 3H), 4.87-4.79 (m, 0.2H), 4.68-4.54 (m, 0.8H), 4.54-4.44 (m, 1H), 4.0-3.47 (m, 4H), 2.47-2.12 (m, 2H). HRMS calc. for $C_{14}H_{18}N_3O_4$ (M+H): 292.1297. found: 292.1294.

Example 2

Synthesis of (2S,4R)-1-(2-Aminoacetyl)-4-benzamidopyrrolidine-2-carboxylic acid hydrochloride Scheme 6

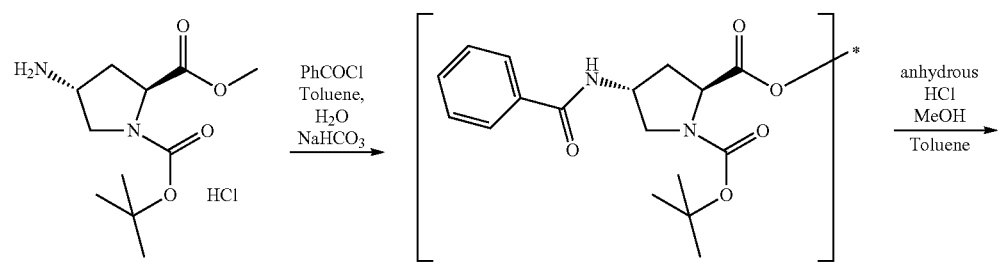

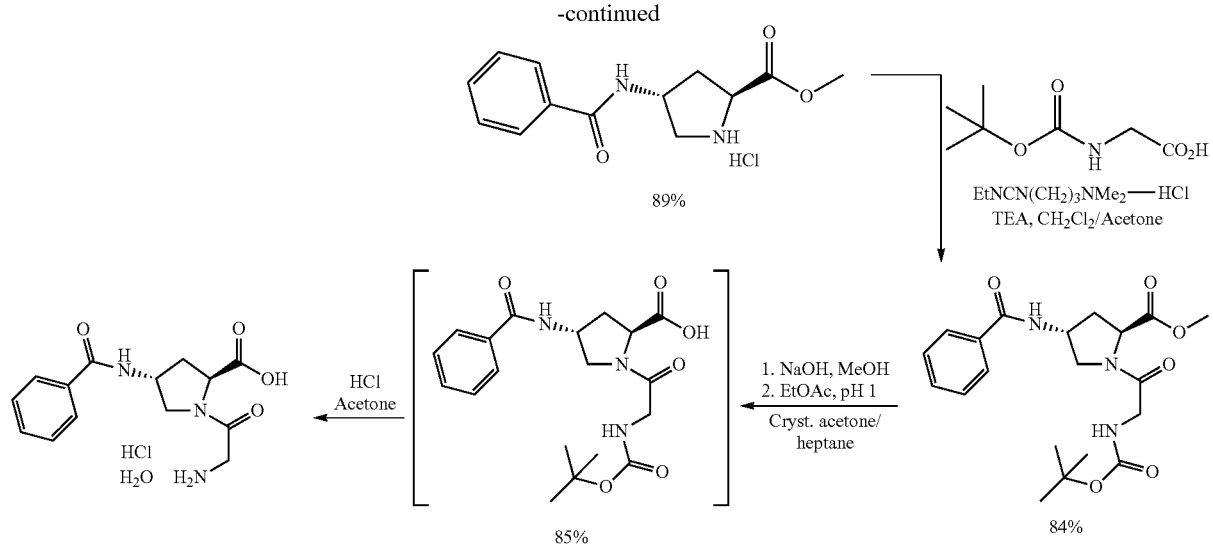

Step 1: Synthesis of (2S,4R)-Methyl 4-benzamidopyrrolidine-2-carboxylate hydrochloride To a 30-L jacketed reactor, with mechanical stirring, was charged 800 g (9.4 moles) of sodium bicarbonate followed by 4.8 kg of water. To this stirred solution was charged N-Boc-trans-4-amino-L-proline methyl ester hydrochloride (0.67 kg) in 3.4 kg of water over 10 minutes. After that, toluene (6.0 kg) (two hazy layers observed) was charged to the 30-L reactor. The reaction mixture was cooled to 0-10° C. with a heating/cooling circulator. Benzoyl chloride (0.328 kg 2.41 moles) in 0.67 kg toluene was charged over 6 min while maintaining temperature between 0-10° C. The transfer line was rinsed with 0.34 kg toluene. The mixture was stirred at 0-10° C. for 3 h and monitored by LC (forms two clear phases). After 3 h, LC showed less than 3% by area of benzoyl chloride. The temperature was adjusted to 20-25° C. The stirring was stopped and the phases were separated. The organic phase was successively extracted with ~1N HCl (1.3 kg), saturated NaHCO$_3$ aqueous solution (3.25 kg), and water (1.3 L mL). The toluene solution was concentrated to 1.5-2.5 L and then chased 2×3.0 kg of toluene. The solution was concentrated to a volume of 2 L at 40-50° C. and 26 in Hg. The concentrate was transferred to a 30-L jacketed reactor with mechanical stirring, under N$_2$ and diluted with 1.8 kg of additional toluene.

To a 2-L 3-neck round bottom flask with a gas inlet tube was charged 0.64 kg MeOH and the flask was weighed (2.15 kg). The MeOH was cooled to –5 to –15° C. in an ice-bath. Anhydrous HCl gas was bubbled for 25 min through the solution. The flask and contents were weighed (2.357 kg). (Calculation: Final weight of contents–Initial weight of contents/volume=g/mL HCl) (2.357 kg–2.15 kg=0.207 kg g/mL HCl).

The MeOH/HCl solution containing (0.207 kg, 5.2 mol, 2.2 eq) was added dropwise over 5 min with stirring, to the toluene solution of the product of step (1) while maintaining the temperature between 15-25° C. After 15 min of stirring, a thick white slurry was observed. The slurry was stirred for 2.5 h at 15-25° C. HPLC indicated the starting material at 2.0%. The slurry was filtered and washed with 2×1.8 L of toluene. The solids were dried at 35-40° C. in vacuum to give, 619 g of product (91% yield from N-Boc-trans-4-amino-L-proline methyl ester hydrochloride). HPLC area percent: 96.3%. NMR conforms to structure. $^1$H NMR (CD$_3$OD, δ, ppm): 7.91-7.84 (m, 2H), 7.6-7.44 (m, 3H), 4.78 (t, J=8.5 Hz, 1H), 4.69-4.59 (m, 1H), 3.77 (dd, J=12, 6.6 Hz, 1H), 3.52 (dd, J=12, 5 Hz, 1H), 2.67-2.5 (m, 2H). MS (m/z, positive ESI, for M+H): 285

Step 2: Synthesis of (2S,4R)-Methyl 4-benzamido-1-(2-(tert-butoxycarbonylamino)acetyl)pyrrolidine-2-carboxylate To a 50-L jacketed reactor equipped with stirrer and temperature probe, was charged (2S,4R)-methyl 4-benzamidopyrrolidine-2-carboxylate hydrochloride (670 g) and methylene chloride (6.7 L) to form white slurry. TEA (230 g) was charged dropwise. The mixture was stirred at 15-25° C. for 15 min to form a clear light yellow solution. Boc-Gly-OH (440 g) and 1-(3-dimethylaminopropyl)-3-ethylcarbodiimide HCl (EDAC) (490 g) were then charged successively while maintaining the reaction mixture temperature below 25° C. The reaction mixture was stirred at 15 to 25° C. for 1 h. HPLC analysis indicated <3% (by area) starting material. Water (3.4 L) was charged to the reaction mixture. The phases were separated. The upper aqueous phase was extracted with methylene chloride (1.8 L). The combined organic phases were successively extracted with 0.5N HCl (1.8 L), 1% of NaHCO$_3$ aqueous solution (1.8 L), and water (1.8 L). Methylene chloride was distilled off at atmospheric pressure and replaced with 10-15 L of acetone. Acetone was distilled off at atmospheric pressure to a volume of about 6 L. The solution was cooled to –5 to –15° C. over 1 h. The product started to crystallize out at ~40° C. The slurry was stirred for 2 h, filtered, washed with heptane (3 kg), and dried to give the product as a white solid, 930 g (85.8% yield, corrected for residual acetone). HPLC area percent: 99.2%. Note: The product is isolated as an acetone solvate. $^1$H NMR (CDCl$_3$, δ, ppm, two conformers): 7.79-7.61 (m, 2H), 7.53-7.39 (m, 3H), 6.85 and 6.69 (two doublets, J=6.4 and 6.8, 1H), 5.32 (br, 1H), 4.84-4.79 (m, 1H), 4.66-4.61 (m, 1H), 4.08-3.91 (m, 2H), 3.78-3.62 (m, 2H), 3.73 (s, 3H), 2.58-2.27 (m, 2H), 1.41 (s, 9H); MS (m/z, positive ESI, for M+Na): 428.

Step 3: Synthesis of (2S,4R)-4-Benzamido-1-(2-(tert-butoxycarbonylamino)acetyl)pyrrolidine-2-carboxylic acid A suspension of (2S,4R)-methyl 4-benzamido-1-(2-(tert-butoxycarbonyl-amino)acetyl)pyrrolidine-2-carboxylate (800 g, 1.97 moles) in MeOH (6.5 L) was heated to 35° C. for dissolution. The solution was cooled to 12° C. A solution of NaOH (prepared from 273 g of 50% aq NaOH and 1.7 kg of water) was added dropwise, while keeping reaction mixture temperature at 10-15° C. The reaction was stirred at 10-15° C. for 1 h and was monitored by HPLC. When the reaction was deemed to be complete (<0.5% of starting material) by HPLC, a solution of 2N HCl (1 L) was added slowly while maintaining the reaction mixture temperature below 20° C. MeOH was removed under vacuum and EtOAc (11.5 L) was charged. More 2N HCl was added to adjust the solution to pH 1-2. The organic phase was separated and washed with water (2×0.8 L). Ethyl acetate was distilled under vacuum until the batch volume reached about 3.5 L. Acetone (6.5 L) was added. Acetone was distilled at atmospheric pressure until the final volume reached about 3.5 L. The mixture was cooled to 45° C. Heptane (3.3 L) was added over 10 min at 45-50° C. The resulting slurry was cooled to room temperature over 30 min, and stirred at room temperature for 1 h. The white solid was filtered and washed with acetone (2×1 L). The wet cake was dried under vacuum to give 650 g of product (85%). The HPLC area purity was >99%. $^1$H NMR (DMSO-$d_6$, δ, ppm, two conformers): 12.6 (bs, 1H), 8.63 and 8.56 (two doublets, J=6.9 Hz, 1H), 7.86-7.82 (m, 2H), 7.57-7.45 (m, 3H), 6.88-6.80 and 6.49 (two multiplets, 1H), 4.66-4.59 (m, 1H), 4.43-4.38 (m, 1H), 3.87-3.64 (m, 3H), 3.48-3.42 (m, 1H), 2.39-2.11 (m, 2H), 1.38 (s, 9H); MS (m/z, positive ESI) for M+H: 392; for M+Na: 41. MS (m/z, positive ESI) for M+H: 392; for M+Na: 414.

Step 4: Synthesis of (2S,4R)-1-(2-Aminoacetyl)-4-benzamidopyrrolidine-2-carboxylic acid hydrochloride To a slurry of (2S,4R)-4-benzamido-1-(2-(tert-butoxycarbonyl-amino)acetyl)pyrrolidine-2-carboxylic acid (650.2 g) in acetone (4.1 L) was added conc. hydrochloric acid (322 g). The reaction mixture was heated to 50° C. over 15 min and stirred at 50° C. The reaction was monitored for completion by HPLC. Water (520 g) was added. The mixture was heated to reflux to dissolve the solid coating. The resulting clear solution was cooled to 40° C. Acetone (7.0 L) was added over 15 min while temperature was maintained at 30-40° C. The mixture was cooled to room temperature over 30 min, and stirred until a white slurry was formed. Additional acetone (7.0 L) was added over 10 min. The mixture was stirred overnight at about 22-24° C. The precipitated solids were filtered through a Buchner funnel lined with polypropylene and washed with acetone (2×2 L), was dried on the funnel to give 530 g (93.8%) of product as a monohydrate. LC area purity was 99.7%. $^1$H NMR (DMSO-$d_6$, δ, ppm, for two conformers): 8.77 (d, J=7 Hz, 0.8H), 8.71 (d, J=7 Hz, 0.2H), 8.68-7.95 (br, 2H), 7.92-7.83 (m, 2H), 7.59-7.43 (m, 3H), 4.87-4.79 (m, 0.2H), 4.68-4.54 (m, 0.8H), 4.54-4.44 (m, 1H), 4.0-3.47 (m, 4H), 2.47-2.12 (m, 2H). HRMS calc. for $C_{14}H_{18}N_3O_4$ (M+H): 292.1297. found: 292.1294.

Example 3

Synthesis of (2S,4S)-1-(2-Aminoacetyl)-4-benzamidopyrrolidine-2-carboxylic acid hydrochloride Scheme 7

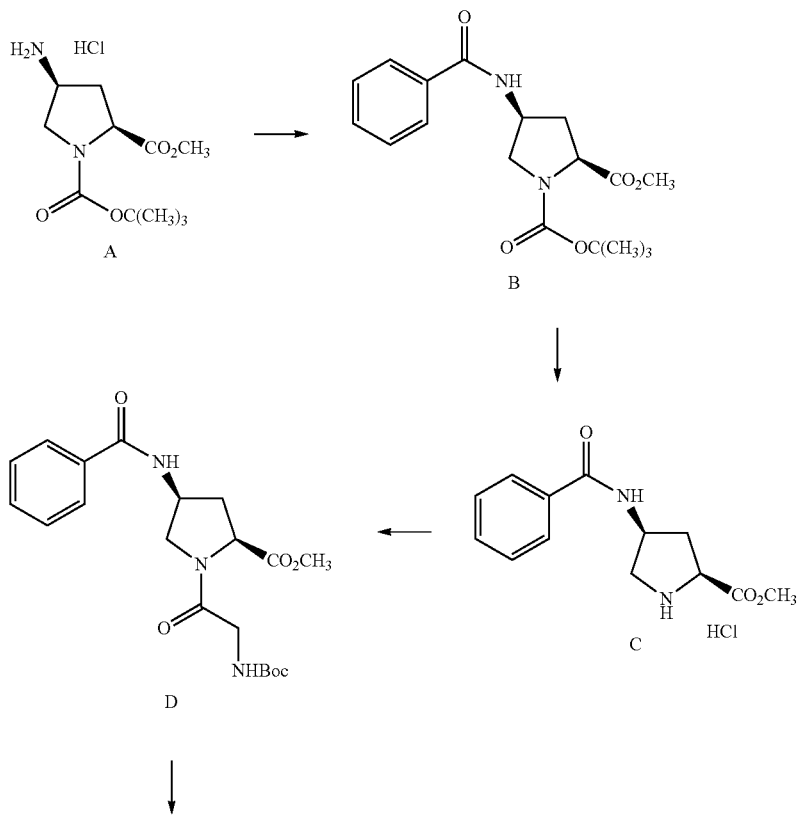

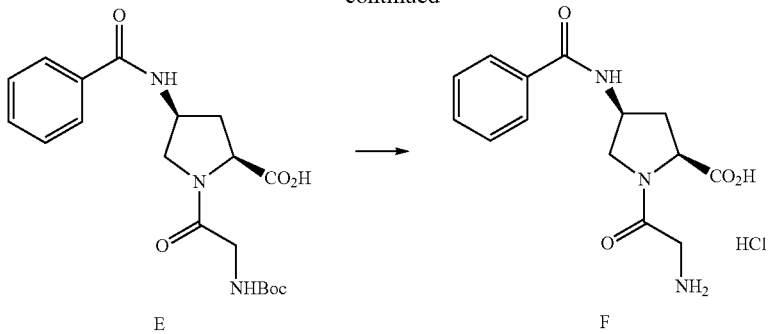

Step 1: Synthesis of (2S,4S)-1-tert-Butyl 2-methyl 4-benzamidopyrrolidine-1,2-dicarboxylate To a 250-mL three-necked round bottom flask, with mechanical stirring, was charged 4.8 g (56.8 mmol) of sodium bicarbonate followed by 48 mL water. To this stirred solution was charged (2S,4S)-1-tert-butyl 2-methyl 4-aminopyrrolidine-1,2-dicarboxylate hydrochloride A (4 g, 14.2 mmol; prepared from commercially available methyl 4-aminopyrrolidine-2-carboxylate) and EtOAc (40 mL) (two hazy layers observed). The reaction mixture was cooled to 5-10° C. with an ice-bath. Benzoyl chloride (2.0 g, 14.2 mmol) in 8 mL EtOAc was charged dropwise over 10 min maintaining temperature between 5-10° C. The mixture was stirred at 5-10° C. for 1 h and monitored by LC, which showed less than 0.5% by area of benzoyl chloride. The stirring was stopped and the phases were separated. The lower aqueous phase was extracted with EtOAc (2×20 mL). The combined EtOAc layer was washed with 1N HCl (20 mL), saturated NaHCO$_3$ aqueous solution (20 mL), brine (20 mL) and dried with Na$_2$SO$_4$. The EtOAc solution was filtered and the filtrate was evaporated to give 4.87 g of (2S,4S)-1-tert-butyl 2-methyl 4-benzamidopyrrolidine-1,2-dicarboxylate B as a white solid (98.2% yield). NMR conforms to structure. HPLC area percent: 99.3%. $^1$H NMR (DMSO-d$_6$, δ, ppm): 8.46 (d, J=6.6 Hz, 1H), 7.81 (d, J=8.1 Hz, 2H), 7.56-7.44 (m, 3 H), 4.48-4.41 (m, 1H), 4.27 (t, J=7.8 Hz, 1H), 3.79-3.71 (m, 1H), 3.69 (d, J=11.7, 3 H). 3.34-3.25 (m, 1H), 2.59-2.50 (m, 1H), 2.08-1.99 (m, 1H), 1.38 (d, J=18.9 Hz, 9H). MS (m/z, positive ESI, for M+H): 349.

Step 2: Synthesis of (2S,4S)-Methyl 4-benzamidopyrrolidine-2-carboxylate

In a 250-mL three-necked round bottom flask, with mechanical stirring, 4.75 g (13.6 mmol) of B was slurried in 20 mL of ether. 50 mL of 2N of HCl in ether was added and the mixture was stirred over night at room temperature. HPLC showed 50% of conversion. 50 mL of 2N HCl in ether was added and stirred for about 60 h at room temperature. No starting material was observed by HPLC. The mixture was filtered, washed with ether, and dried in a funnel, to give 3.85 g of white solid (2S,4S)-methyl 4-benzamidopyrrolidine-2-carboxylate C (99.4% yield). NMR conforms to structure. HPLC area percent: 97.9%. $^1$H NMR (DMSO-d$_6$, δ, ppm): 8.82 (d, J=6.3 Hz 1H), 7.88 (d, J=8.4 Hz 2H), 7.58-7.46 (m, 3H), 4.64-4.50 (m, 2H), 3.78 (s, 3H), 3.52-3.46 (m, 1H), 3.36-3.30 (m, 1H), 2.72 (m, 1H), 2.26-2.17 (m, 1H). MS (m/z, positive ESI, for M+H): 249.

Step 3: Synthesis of (2S,4S)-Methyl 4-benzamido-1-(2-(tert-butoxycarbonylamino)acetyl)pyrrolidine-2-carboxylate hydrochloride To a 250-mL three-necked round bottom flask, was charged C (2.5 g) and EtOAc (50 mL) to form white slurry. TEA (2.5 mL) was charged dropwise. The mixture was stirred at 15-25° C. for 10 min to form a clear light yellow solution. Boc-Gly-OH (1.85 g) and EDAC (2.01 g) were then charged successively while maintaining the reaction mixture temperature below 25° C. (Note: moderate exotherm was observed). The reaction mixture was stirred at 15 to 25° C. for 1 h. The reaction was deemed to be complete by HPLC analysis. Water (50 mL) was charged. The phases were separated. The aqueous phase was back extracted with EtOAc (2×25 mL). The combined organic phase was successively washed with 2 N HCl (25 mL), saturated NaHCO$_3$ aqueous solution (25 mL) and brine (25 mL). The organic phase was dried over Na$_2$SO$_4$ and concentrated under vacuum and to give 3.35 g (2S,4S)-methyl 4-benzamido-1-(2-(tert-butoxycarbonylamino)acetyl)pyrrolidine-2-carboxylate hydrochloride D as a white solid (94.1% yield). NMR conforms to structure. HPLC area percent: 99.4%. $^1$H NMR (DMSO-d$_6$, δ, ppm): 8.49 (d, J=6 Hz, 0.8H), 8.32 (d, J=6 Hz, 0.2H), 7.84-7.76 (m, 2 H), 7.57-7.45 (m, 3H), 6.90-6.86 (m, 1H), 4.60-4.54 (q, J=6 Hz, 1H), 4.35 (t, J=6 Hz, 1H), 3.88-3.62 (m, 3H), 3.62 (s, 3H), 3.52-3.43 (m, 1H), 2.55-2.46 (m, 1H), 2.05-1.96 (m, 1H), 1.38 (s, 9H). MS (m/z, positive ESI, for M+Na): 428.

Step 4: Synthesis of (2S,4S)-4-Benzamido-1-(2-(tert-butoxycarbonylamino)acetyl)pyrrolidine-2-carboxylic acid A solution of D (3.2 g) in MeOH (50 mL) was cooled to −5 to 0° C. A solution of 2 N NaOH (20 mL) was added dropwise, while keeping reaction mixture temperature below 0° C. The reaction was stirred at about 0° C. and was monitored by HPLC. When the reaction was deemed to be complete by HPLC, a solution of 2N HCl (20 mL) was added slowly while maintaining the reaction mixture temperature below 0° C. MeOH was removed under vacuum and EtOAc (50 mL) was charged. The phases were separated and the aqueous phase was extracted with EtOAc (2×25 mL). The combined EtOAc phase was dried over Na$_2$SO$_4$ and concentrated under vacuum and to give 2.9 g (2S,4S)-4-benzamido-1-(2-(tert-butoxycarbonylamino)acetyl)pyrrolidine-2-carboxylic acid E as a white solid (94% yield). NMR conforms to structure. HPLC area percent: 98.7%. $^1$H NMR (DMSO-d$_6$, δ, ppm): 8.46 (d, J=6.9 Hz, 0.8H), 8.35 (d, J=6 Hz, 0.2H), 7.84-7.78 (m, 2H), 7.57-7.43 (m, 3 H), 6.88-6.81 (m, 1H), 4.58-4.52 (q, J=6 Hz, 1H), 4.24 (t, J=9 Hz, 1H), 3.92-3.65 (m, 3H), 3.49-3.43 (m, 1H), 2.54-2.45 (m, 1H), 2.08-1.99 (m, 1H), 1.38 (s, 9H). MS (m/z, positive ESI): M+Na: 414.

Step 5: Synthesis of (2S,4S)-1-(2-Aminoacetyl)-4-benzamidopyrrolidine-2-carboxylic acid hydrochloride A solution of E (2.5 g) in acetone (25 mL) was stirred. Concentrated HCl (1.26 g) was added to the hazy reaction mixture at room temperature. The reaction was stirred at 48-50° C. and was monitored by HPLC. After 1 h, solids were found adhering to the walls of the flask. An additional 25 mL of acetone was added and the heating continued at 45-50° C. After 3 h, all the solids from the wall were suspended a slurry was obtained. When the reaction was deemed to be complete by HPLC (5 h) the reaction mixture temperature was cooled to 25° C. The precipitated solids were filtered through a Buchner funnel lined with polypropylene and washed with acetone (2×5 mL). The product (2S,4S)-1-(2-aminoacetyl)-4-benzamidopyrrolidine-2-carboxylic acid hydrochloride F was air dried to give 1.8 g (86% yield). NMR conforms to structure. HPLC area percent: 95.8%. $^1$H NMR (DMSO-$d_6$, δ, ppm, for two conformers): 8.46 (d, J=6.9 Hz, 0.8H), 8.33 (d, J=6 Hz, 0.2H), 7.84-7.7.78 (m, 2H), 7.54-7.44 (m, 3H), 6.87-6.78 (m, 1H), 4.59-4.52 (m, 1H), 4.29-4.24 (m, 1H), 3.92-3.66 (m, 3H), 3.51-3.44 (m, 1H), 2.55-2.45 (m, 1H), 2.05-1.97 (m, 1H), 1.38 (s, 9H).

Example 4

Synthesis of (2S,4R)-Methyl 4-benzamidopyrrolidine-2-carboxylate hydrochloride (Methyl (4R)-4-(benzoylamino)-L-prolinate hydrochloride)

Step 1: Synthesis of 1-Benzyl 2-methyl (2S,4S)-4-hydroxypyrrolidine-1,2-dicarboxylate

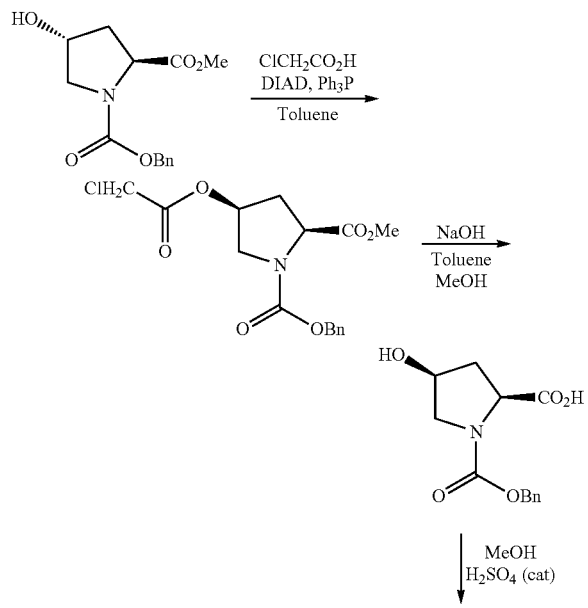

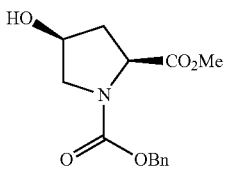

1-Benzyl 2-methyl (2S,4R)-4-hydroxypyrrolidine-1,2-dicarboxylate was prepared from commercially available trans-4-hydroxy-L-proline based on literature references (e.g., Bridges et al. *J. Med. Chem.* 1991, 34, 717; Gregson et al. *J. Med. Chem.* 2004, 47, 1161). A solution of 1-benzyl 2-methyl (2S,4R)-4-hydroxypyrrolidine-1,2-dicarboxylate (trans-4-hydroxy-N-Cbz-L-proline methyl ester, 15 g, 53.7 mmol), chloroacetic acid (8.4 g, 88.6 mmol), and triphenyl phosphine (23.2 g, 88.6 mmol) in toluene (100 mL) was cooled to 0-10° C., with mechanical stirring. To this stirred solution was slowly charged DIAD (17.9 g, 88.6 mmol) while maintaining the temperature of the reaction mixture 0-10° C. The reaction mixture was warmed to room temperature and was stirred at room temperature for 16 h.

The stirred the reaction mixture was cooled to 0-10° C. and was charged with methanol (40 mL). To the stirred reaction mixture was charged 5 N NaOH (40 mL) while maintaining the reaction temperature 0-10° C. The reaction mixture is stirred at 0-10° C. for 2 h. Phases were separated. The aqueous phase was extracted with toluene (4×30 mL). The aqueous phase was cooled to 0-10° C. and was acidified with concentrated HCl (18 mL) to pH 2. The acidified aqueous solution was extracted with ethyl acetate (3×40 mL). The combined ethyl acetate solution was concentrated under vacuum to give 23 g of an oil.

The oil was dissolved in methanol (150 mL). The stirred solution was charged with concentrated sulfuric acid (1 mL). The mixture was heated at reflux for 6 h. The mixture was concentrated to about 75 mL. An aqueous solution of sodium bicarbonate (75 mL, prepared from 10 mL of saturated sodium bicarbonate and 65 mL of water) was charged dropwise, followed by the addition of water (150 mL). The slurry was stirred at room temperature for 0.5 h. The slurry was filtered and the wet cake was dried under vacuum (40° C.) for 16 h to afford 9.0 g of the title compound (60% yield). $^1$H NMR (CDCl$_3$, δ, ppm): 7.61-7.09 (m, 5H), 5.42-5.04 (m, 2H), 4.47-4.38 (m, 2H), 3.81-3.57 (m, 5H), 3.37-3.20 (m, 1H), 2.39-2.11 (m, 2H). MS (m/z, positive ESI, for M+H): 280.

Step 2: Synthesis of 1-Benzyl 2-methyl (2S,4R)-4-aminopyrrolidine-1,2-dicarboxylate Method A

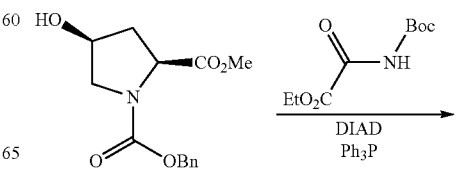

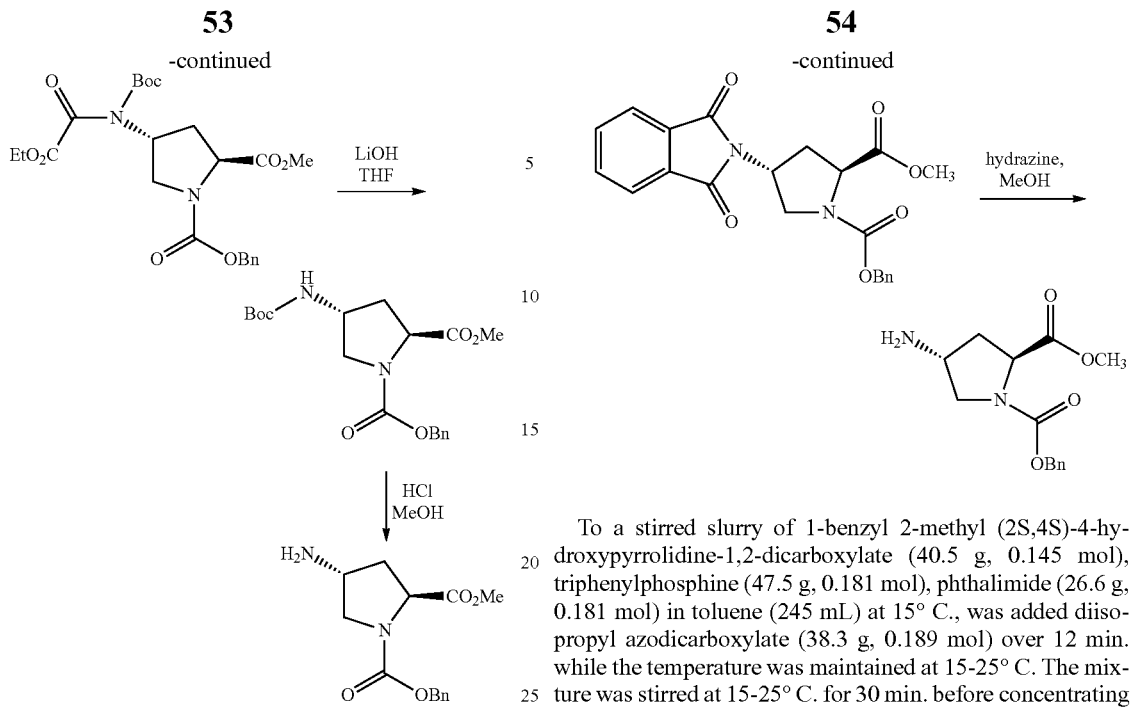

A solution of 1-benzyl 2-methyl (2S,4S)-4-hydroxypyrrolidine-1,2-dicarboxylate (2.0 g, 7.2 mmol.), triphenylphosphine (2.8 g, 10.7 mmol), N-Boc-ethyl oxamate (2.3 g, 10.7 mmol) in THF (20 mL) was cooled to 0-10° C. To the stirred solution was charged DIAD (2.2 g, 10.7 mmol) while maintaining the reaction temperature 0-10° C. The reaction was stirred at 0-15° C. for 3 h.

A solution of lithium hydroxide monohydrate (0.9 g, 21.5 mmol) in water (100 mL) was charged while maintaining the reaction temperature 0-10° C. The reaction was stirred at 0-10° C. for 1 h. The reaction was diluted with water (10 mL) and ethyl acetate (30 mL). The phases were separated. The organic phase was extracted with water (15 mL) and brine (15 mL).

The ethyl acetate solution was concentrated under vacuum and the resulting residue was dissolved in toluene (20 mL). To the stirred solution was charged methanol (6 mL) and acetyl chloride (1 mL). The mixture was stirred at room temperature for 16 h. The reaction mixture is diluted with 0.5 N HCl (30 mL). The phases were separated. The toluene phase was extracted with 0.5 N HCl (15 mL). The combined aqueous phase was extracted with EtOAc (3×30 mL).

The above aqueous solution was cooled to 0-10° C. and was basified with 10 N NaOH to pH 11. The aqueous solution was extracted with EtOAc (3×30 mL). The combined aqueous phase was dried over MgSO$_4$ and concentrated under vacuum to afford the title compound as a yellow oil, 0.5 g (25% yield).

Method B:

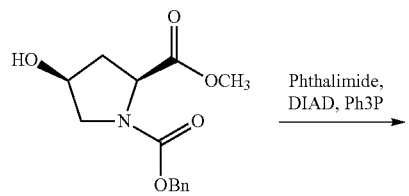

To a stirred slurry of 1-benzyl 2-methyl (2S,4S)-4-hydroxypyrrolidine-1,2-dicarboxylate (40.5 g, 0.145 mol), triphenylphosphine (47.5 g, 0.181 mol), phthalimide (26.6 g, 0.181 mol) in toluene (245 mL) at 15° C., was added diisopropyl azodicarboxylate (38.3 g, 0.189 mol) over 12 min. while the temperature was maintained at 15-25° C. The mixture was stirred at 15-25° C. for 30 min. before concentrating to about 250 mL. The concentrate was then cooled to 0-5° C. in an ice-bath, and stirred at the same temperature for 2 h. The precipitated solid was filtered, washed with cold toluene (100 mL), and discarded. The filtrate was washed with 0.1 N aqueous sodium hydroxide solution (2×200 mL), and then with water (100 mL). The organic phase was concentrated to a residue of about 130 g crude (2S,4R)-1-benzyl 2-methyl 4-(1,3-dioxoisoindolin-2-yl)pyrrolidine-1,2-dicarboxylate in toluene. A small analytical sample was purified by silica gel chromatography. $^1$H NMR (300 MHz, CDCl$_3$) δ 7.86-7.83 (m, 2H), 7.77-7.72 (m, 2H), 7.39-7.29 (m, 5H), 5.26-5.00 (m, 3H), 4.71-4.66 (m, 1H), 3.95-3.90 (m, 2H), 3.79, 3.63 (two s, 3H), 3.10-2.99 (m, 1H), 2.29-2.20 (m, 1H).

Other solvents such as tetrahydrofuran, dichloromethane, ethyl acetate may substituted for toluene effectively. The reaction may be run at a range from about −5 to 35° C. with little effect on results.

The above toluene solution was transferred to a 2-L flask with 30 mL of toluene rinse. The solution was diluted with methanol (800 mL). To the diluted solution was added hydrazine hydrate (20.5 g, 0.347 mol). After stirring at 20-25° C. for 10 min, the mixture was heated to 55-60° C. over 15 min. and maintained at the same temperature for 3 h. HPLC showed that the reaction was complete. The mixture was cooled to 20-25° C. before water (30 g) was added to facilitate stirring. The fluffy solid was filtered, washed with toluene (100 mL) and discarded. The filtrate was acidified to pH 3 with 4 N HCl (about 65 mL). The acidic mixture was concentrated under vacuum to a residual volume of about 200 mL, and further acidified with hydrochloric acid to pH ~1. Dichloromethane (170 mL) and water (65 mL) were added to the above concentrate with efficient stirring. The organic phase was separated, extracted with water (50 mL) and discarded. The combined aqueous phases were washed with dichloromethane (170 mL), and then diluted with more dichloromethane (150 mL). The biphasic mixture was neutralized with 5 N aqueous sodium hydroxide solution to pH ~12. The aqueous phase was separated, and extracted with dichloromethane (150 mL). The combined organic phases were washed with 0.025 N aqueous sodium hydroxide (100 mL) and then with water (50 mL). The final organic phase was concentrated to give 1-benzyl 2-methyl (2S,4R)-4-aminopyrrolidine-1,2-carboxylate as an oil (26.8 g, 66% overall yield from 1-benzyl 2-methyl (2S,4S)-4-hydroxypyrrolidine-1,2-dicarboxylate). NMR (CDCl$_3$, δ, ppm): 7.62-7.08 (m, 5H), 5.40-4.99 (m, 2H), 4.50-4.44 (m, 1H), 3.81-3.57 (m, 5H), 3.30-3.18 (m, 1H), 2.19-1.81 (m, 2H), 1.30-1.25 (m, 2H). MS (m/z, positive ESI, for M+H): 279.

The reaction is generally most effective in alcoholic solvents such as methanol, ethanol or propanol, but other solvents such as tetrahydrofuran, acetonitrile also give satisfactory results. Reaction temperatures may vary up to boiling points of solvents used.

Step 3: Synthesis of (2S,4R)-Methyl 4-benzamidopyrrolidine-2-carboxylate hydrochloride (Methyl (4R)-4-(benzoylamino)-L-prolinate hydrochloride)

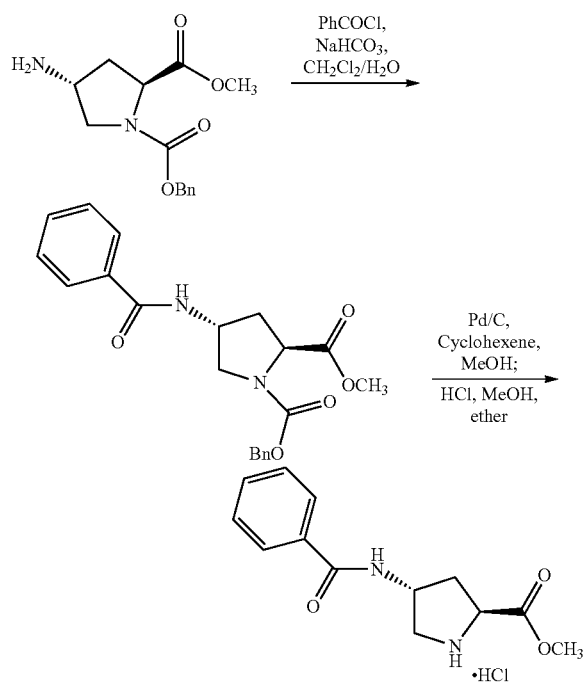

To a solution of 1-benzyl 2-methyl (2S,4R)-4-aminopyrrolidine-1,2-dicarboxylate (26.8 g, 0.096 mol) in dichloromethane (75 mL) at 0-5° C., were charged water (140 mL) and sodium bicarbonate (20.2 g, 0.24 mol), followed by slow addition of benzoyl chloride (13.4 g, 0.095 mol) in dichloromethane (50 mL) while the temperature was maintained at 0-10° C. After stirring for 5 min, the mixture was warmed to 20-25° C. Water (60 mL) was added to dissolve the solid. The organic phase was separated and washed with 1 N hydrochloric acid (25 mL), 5% aqueous sodium bicarbonate (30 mL), and water (55 mL). The organic phase was distilled, and dichloromethane was replaced with methanol to give 75 g of a residual concentrate. A small sample of the product, (2S,4R)-1-benzyl 2-methyl 4-benzamidopyrrolidine-1,2-dicarboxylate, was taken out for analysis. $^1$H NMR (300 MHz, CDCl$_3$) δ 7.81-7.72 (m, 2H), 7.52-7.19 (m, 8H), 6.48-6.40 (m, 1H), 5.21-4.99 (m, 2H), 4.77-4.74 (m, 1H), 4.52-4.45 (m, 1H), 3.98-3.89 (m, 1H), 3.74, 3.59 (two s, 3H), 3.58-3.47 (m, 1H), 2.41-2.26 (m, 2H).

In this reaction, solvents such as toluene, ethyl acetate, or tetrahydrofuran may substituted for dichloromethane. This transformation may also be performed under non-aqueous conditions using bases such as triethylamine, N,N-diisopropylethylamine.

To the above methanol concentrate of (2S,4R)-1-benzyl 2-methyl 4-benzamidopyrrolidine-1,2-dicarboxylate, were added a slurry of 10% Pd/C (dry, 4.1 g) in methanol (100 mL) and cyclohexene (80 mL). The mixture was heated at reflux (57° C.) for 7 h. before being cooled to 20-25° C. Palladium catalyst was filtered off through a pad of Celite, and washed with methanol. The filtrate was concentrated, and cyclohexene was removed as a methanol azetrope. To the final methanol solution was added 1 N hydrogen chloride in diethyl ether (110 mL, 0.11 mol) while the temperature was maintained at 20-25° C. The resulting slurry was cooled to 10-15° C. over 20 min. The solid product was filtered and washed with toluene. The wet solid was dried at 60° C. under vacuum to give 22.4 g of (2S,4R)-methyl 4-benzamidopyrrolidine-2-carboxylate hydrochloride as white solid (81.7% overall yield from 1-benzyl 2-methyl (2S,4R)-4-aminopyrrolidine-1,2-dicarboxylate). $^1$H NMR (CDCl$_3$, δ, ppm): 9.99 (bs, 2H), 8.95 (d, J=6.6 Hz, 1H), 7.97-7.94 (m, 2H), 7.58-7.45 (m,3H), 4.71 (t, J=8.7 Hz, 1H), 4.68-4.61 (m 1H), 3.78 (s, 3H), 3.58 (dd, J=11.9, 6.6 Hz, 1H), 3.32 (dd, J=11.9, 4.2 Hz, 1H), 2.41 (d, J=8.6 Hz, 1H), 2.39 (d, J=8.6 Hz, 1H).

Cyclohexene may be replaced by other hydrogen transfer agents such as 2-methyl-cyclohexene, cyclohexadiene, ammonium formate. The benzyloxycarbonyl group may also be removed by catalytic hydrogenation.

Example 5

Preparation of crystalline (2S,4R)-1-(2-aminoacetyl)-4-benzamidopyrrolidine-2-carboxylic acid hydrochloride monohydrate Method 1:

32 mg of amorphous (2S,4R)-1-(2-aminoacetyl)-4-benzamidopyrrolidine-2-carboxylic acid hydrochloride was dissolved in three volumes of an isopropanol/water (19.5:0.5 ratio by volume) mixed solvent at room temperature. The container was left open, and the crystals that had formed were collected. The crystalline solid was dried at 40-50° C. under vacuum to give crystalline (2S,4R)-1-(2-aminoacetyl)-4-benzamidopyrrolidine-2-carboxylic acid hydrochloride monohydrate.

Method 2

60.5 mg of amorphous (2S,4R)-1-(2-aminoacetyl)-4-benzamidopyrrolidine-2-carboxylic acid hydrochloride was dissolved in 0.3 mL isopropanol/t-butyl methyl ether (7:3 ratio by volume) and 2.0 mL acetone/water (19:1 ratio by volume) mixed solvent system at room temperature. The container was left open, and the crystals that had formed were collected. The crystalline solid was dried at 40-50° C. under vacuum to give crystalline (2S,4R)-1-(2-aminoacetyl)-4-benzamidopyrrolidine-2-carboxylic acid hydrochloride monohydrate.

Method 3

36.5 mg of amorphous (2S,4R)-1-(2-aminoacetyl)-4-benzamidopyrrolidine-2-carboxylic acid hydrochloride was dissolved in 0.5 mL of an acetone/water (19.5:0.5 by volume) mixed solvent at room temperature. The container was stirred and the crystals that had formed were collected. The crystalline solid was dried at 40-50° C. under vacuum to give crystalline (2S,4R)-1-(2-aminoacetyl)-4-benzamidopyrrolidine-2-carboxylic acid hydrochloride monohydrate.

Other embodiments of the present disclosure will be apparent to those skilled in the art from consideration of the specification and practice of the information disclosed herein. It is intended that the specification and examples be considered as exemplary only, with a true scope and spirit of the present disclosure being indicated by the following claims.

What is claimed is:

1. A compound that is (2S,4R)-1-(2-aminoacetyl)-4-benzamidopyrrolidine-2-carboxylic acid hydrochloride monohydrate.

2. The compound of claim 1, having an X-ray powder diffraction pattern substantially as in FIG. 2.

3. A pharmaceutical formulation comprising one or more pharmaceutically acceptable carriers and a compound of claim 1.

* * * * *